US011274154B2

(12) United States Patent
Andrews et al.

(10) Patent No.: US 11,274,154 B2
(45) Date of Patent: Mar. 15, 2022

(54) DOSING REGIMEN OF AVELUMAB FOR THE TREATMENT OF CANCER

(71) Applicants: PFIZER INC., New York, NY (US); MERCK PATENT GmbH, Darmstadt (DE)

(72) Inventors: Glen Ian Andrews, San Diego, CA (US); Carlo Leonel Bello, San Francisco, CA (US); Satjit Singh Brar, San Diego, CA (US); Shaonan Wang, Muehltal-Traisa (DE); Pascal Girard, Renens (CH)

(73) Assignees: PFIZER INC., New York, NY (US); MERCK PATENT GMBH, Darmstadt (DE)

( * ) Notice: Subject to any disclaimer, the term of this patent is extended or adjusted under 35 U.S.C. 154(b) by 255 days.

(21) Appl. No.: 16/339,779

(22) PCT Filed: Oct. 5, 2017

(86) PCT No.: PCT/IB2017/056160
§ 371 (c)(1),
(2) Date: Apr. 5, 2019

(87) PCT Pub. No.: WO2018/065938
PCT Pub. Date: Apr. 12, 2018

(65) Prior Publication Data
US 2019/0330352 A1    Oct. 31, 2019

Related U.S. Application Data

(60) Provisional application No. 62/405,188, filed on Oct. 6, 2016, provisional application No. 62/565,728, filed on Sep. 29, 2017.

(51) Int. Cl.
*C07K 16/28* (2006.01)
*A61K 39/395* (2006.01)
*A61P 35/00* (2006.01)

(52) U.S. Cl.
CPC .......... *C07K 16/2827* (2013.01); *A61P 35/00* (2018.01); *C07K 2317/14* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly |
| 5,545,806 A | 8/1996 | Lonberg |
| 5,545,807 A | 8/1996 | Sumni |
| 5,569,825 A | 10/1996 | Lonberg |
| 5,625,126 A | 4/1997 | Lonberg |
| 5,633,425 A | 5/1997 | Lonberg |
| 5,641,870 A | 6/1997 | Rinderknecht |
| 5,661,061 A | 8/1997 | Usuami |
| 6,075,181 A | 6/2000 | Kucherlapati |
| 6,150,584 A | 11/2000 | Kucherlapati |
| 6,534,524 B1 | 3/2003 | Kania |
| 6,884,890 B2 | 4/2005 | Kania |
| 6,982,321 B2 | 1/2006 | Winter |
| 7,087,409 B2 | 8/2006 | Barbas |
| 7,141,581 B2 | 11/2006 | Bender |
| 7,232,910 B2 | 6/2007 | Ewanicki |
| 7,326,414 B2 | 2/2008 | Bedian |
| 7,488,802 B2 | 2/2009 | Collins |
| 7,521,051 B2 | 4/2009 | Collins |
| 7,794,710 B2 | 9/2010 | Chen |
| 7,960,515 B2 | 6/2011 | Min |
| 8,008,449 B2 | 8/2011 | Korman |
| 8,168,757 B2 | 5/2012 | Finnefmck |
| 8,337,850 B2 | 12/2012 | Ahrens |
| 8,354,509 B2 | 1/2013 | Careen |
| 8,383,796 B2 | 2/2013 | Korman |
| 8,552,154 B2 | 10/2013 | Freeman |
| 8,779,108 B2 | 7/2014 | Queva |
| 8,791,140 B2 | 7/2014 | Campeta |
| 8,993,731 B2 | 3/2015 | Tyson |
| 9,045,545 B1 | 6/2015 | Clube |
| 9,073,994 B2 | 7/2015 | Honjo |
| 9,457,019 B2 | 10/2016 | Flynn |
| 9,539,245 B2 | 1/2017 | Peters |
| 9,624,298 B2 | 4/2017 | Nastri |
| 9,682,143 B2 | 6/2017 | Chang |
| 9,683,048 B2 | 6/2017 | Freeman |
| 9,765,147 B2 | 9/2017 | Wong |
| 9,993,551 B2 | 6/2018 | Lebwohl |

(Continued)

FOREIGN PATENT DOCUMENTS

| | | |
|---|---|---|
| EP | 0404097 | 12/1990 |
| WO | WO1991010741 | 7/1991 |

(Continued)

OTHER PUBLICATIONS

Ahmadzadeh, et al., Tumor antigen-specific CD8 T cells infiltrating the tumor express high levels of PD-1 and are functionally impaired, Blood, 114(8):1537-44 (2009).

Anonymous, "Avelumab in Metastatic or Locally Advanced Solid Tumors," (Javelin Solid Tumor)—Full Text View—ClinicalTrials. gov, Jan. 14, 2013, URL:https://clinicaltrials.gov/ct2/show/NC T01772004?term=Avelumab&cond=HNSCC&rank=5 [retrieved on Jun. 23, 2017] the whole document (12 pages).

Anonymous, "Avelumab In Patients With Previously Treated Advanced Stage Classical Hodgkin's Lymphoma (Javelin Hodgkins)—Full Text View—ClinicalTrials.gov", Nov. 9, 2015 (Nov. 9, 2015), XP055384712, Retrieved from the Internet: URL:https://clinicaltrials. gov/ct2/show/NC T02603419?term=Avelumab&draw-l&rank=38 [retrieved on Jun. 23, 2017] the whole document (10 pages).

(Continued)

*Primary Examiner* — Ilia I Ouspenski
(74) *Attorney, Agent, or Firm* — Haley Guiliano LLP; James F. Haley, Jr.

(57) ABSTRACT

The present invention relates to dosing regimen of avelumab for the treatment of cancer. In particular, the invention relates to improved dosing regimen of avelumab for the treatment of cancer.

20 Claims, 13 Drawing Sheets
Specification includes a Sequence Listing.

(56) References Cited

U.S. PATENT DOCUMENTS

| | | | |
|---|---|---|---|
| 10,004,755 B2 | 6/2018 | Wang | |
| 10,138,299 B2 | 11/2018 | Cogswell | |
| 10,323,092 B2 | 6/2019 | Cogswell | |
| 10,487,147 B2 | 11/2019 | Nastri | |
| 10,570,202 B2 | 2/2020 | Martini | |
| 2004/0224988 A1 | 11/2004 | Freddo | |
| 2006/0091067 A1 | 5/2006 | Fan | |
| 2006/0094763 A1 | 5/2006 | Ye | |
| 2007/0203196 A1 | 8/2007 | Ewanicki | |
| 2008/0274192 A1 | 11/2008 | Friesen | |
| 2010/0179329 A1 | 7/2010 | Campeta | |
| 2012/0089541 A1 | 4/2012 | Patel | |
| 2013/0078240 A1 | 3/2013 | Ahrens | |
| 2013/0309250 A1 | 11/2013 | Cogswell | |
| 2014/0242071 A1 | 8/2014 | Liu | |
| 2014/0248347 A1 | 9/2014 | Morgado | |
| 2014/0288125 A1 | 9/2014 | Murray | |
| 2014/0341917 A1* | 11/2014 | Nastri | A61K 39/0011 424/139.1 |
| 2015/0190506 A1 | 7/2015 | Cheung | |
| 2015/0210769 A1 | 7/2015 | Freeman | |
| 2015/0210772 A1* | 7/2015 | Kim | C07K 16/2887 424/135.1 |
| 2015/0273033 A1 | 10/2015 | Bosch | |
| 2016/0009805 A1 | 1/2016 | Kowanetz | |
| 2016/0067336 A1* | 3/2016 | Fandi | A61K 39/395 424/133.1 |
| 2016/0083401 A1 | 3/2016 | Fuchss | |
| 2016/0108123 A1 | 4/2016 | Freeman | |
| 2016/0152715 A1 | 6/2016 | Wong | |
| 2016/0159905 A1 | 6/2016 | Abdiche | |
| 2017/0000885 A1* | 1/2017 | Rhee | C07K 16/2827 |
| 2017/0008971 A1 | 1/2017 | Dennis | |
| 2017/0037132 A1* | 2/2017 | Manekas | C12Q 1/6886 |
| 2017/0088626 A1 | 3/2017 | Jure-Kunkel | |
| 2017/0158776 A1 | 6/2017 | Feltquate | |
| 2017/0166641 A1 | 6/2017 | Martini | |
| 2017/0209574 A1 | 7/2017 | Cao | |
| 2017/0266280 A1* | 9/2017 | Rastelli | A61K 39/39541 |
| 2017/0296659 A1 | 10/2017 | Lebwohl | |
| 2017/0298106 A1 | 10/2017 | Roschke | |
| 2017/0320930 A1 | 11/2017 | Matzke-Ogi | |
| 2017/0340733 A1* | 11/2017 | Cao | A61K 31/404 |
| 2018/0000931 A1* | 1/2018 | Bacac | C07K 16/30 |
| 2018/0162941 A1 | 6/2018 | Thanavala | |
| 2018/0162942 A1 | 6/2018 | Simon | |
| 2018/0169232 A1* | 6/2018 | Andrews | A61K 39/39558 |
| 2018/0186882 A1 | 7/2018 | Freeman | |
| 2018/0200338 A1* | 7/2018 | Umana | A61K 47/6813 |
| 2018/0244781 A1 | 8/2018 | Cuillerot | |
| 2018/0264004 A1* | 9/2018 | Karin | A61K 31/136 |
| 2018/0282415 A1 | 10/2018 | Lin | |
| 2018/0289771 A1* | 10/2018 | Shan | A61K 31/337 |
| 2018/0326010 A1* | 11/2018 | Codarri Deak | A61K 47/6813 |
| 2018/0353602 A1* | 12/2018 | Goodenow | G01N 33/57415 |
| 2019/0000944 A1* | 1/2019 | Brogdon | A61K 39/0011 |
| 2019/0144545 A1* | 5/2019 | Nuyten | A61P 35/04 424/142.1 |
| 2019/0161549 A1* | 5/2019 | Choong | A61P 35/04 |
| 2019/0211104 A1* | 7/2019 | Wilm | C07K 16/30 |
| 2020/0048352 A1 | 2/2020 | Zimmermann | |
| 2020/0254091 A1* | 8/2020 | Blake-Haskins | A61K 31/5025 |
| 2021/0077463 A1* | 3/2021 | Boshoff | A61K 9/0053 |
| 2021/0085683 A1* | 3/2021 | Briere | A61P 35/04 |

FOREIGN PATENT DOCUMENTS

| | | |
|---|---|---|
| WO | WO1993011161 | 6/1993 |
| WO | WO1996033735 | 10/1996 |
| WO | WO1996034096 | 10/1996 |
| WO | WO1998024893 | 6/1998 |
| WO | WO2004072286 | 8/2001 |
| WO | WO2004004771 | 1/2004 |
| WO | WO2004056875 | 7/2004 |
| WO | WO2006048745 | 5/2006 |
| WO | WO2007005874 | 1/2007 |
| WO | WO2008100562 | 8/2008 |
| WO | WO2008156712 | 12/2008 |
| WO | WO2010027827 | 3/2010 |
| WO | WO2010036959 | 4/2010 |
| WO | WO2010077634 | 7/2010 |
| WO | WO2010089411 | 8/2010 |
| WO | WO2011066342 | 6/2011 |
| WO | WO2011068561 | 6/2011 |
| WO | WO2013019906 | 2/2013 |
| WO | WO2013028231 | 2/2013 |
| WO | WO2013046133 | 4/2013 |
| WO | WO2013079174 | 6/2013 |
| WO | WO2013119202 | 8/2013 |
| WO | WO2013164754 | 11/2013 |
| WO | WO2013181452 | 12/2013 |
| WO | WO2014100079 | 6/2014 |
| WO | WO2014163684 | 10/2014 |
| WO | WO2014167088 | 10/2014 |
| WO | WO2015036511 | 3/2015 |
| WO | WO2015061668 | 4/2015 |
| WO | WO2015069266 | 5/2015 |
| WO | WO2015088847 | 6/2015 |
| WO | WO2015095410 | 6/2015 |
| WO | WO2015095423 | 6/2015 |
| WO | WO2014151006 | 9/2015 |
| WO | WO2015134605 | 9/2015 |
| WO | WO2016014148 | 1/2016 |
| WO | WO2016032927 | 3/2016 |
| WO | WO2016059602 | 4/2016 |
| WO | WO2016081384 | 5/2016 |
| WO | WO2016089873 | 6/2016 |
| WO | WO2016100882 | 6/2016 |
| WO | WO2016137985 | 9/2016 |
| WO | WO2016205277 | 12/2016 |
| WO | WO2015036499 | 3/2017 |
| WO | WO2017197140 | 11/2017 |

OTHER PUBLICATIONS

Anonymous, "Avelumab in Previously Untreated Patients With Epithelial Ovarian Cancer (Javelin Ovarian 100)—Full Text View—ClinicalTrials.gov", Mar. 12, 2016 (Mar. 15, 2016), XP055384715, Retrieved from the Internet: URL:https://clinicaltrials.gov/ct2/show/NCT02718417?term=Avelumab&draw-1&rank=41 [retrieved on Jun. 23, 2017] the whole document (11 pages).

Anonymous, "History of Changes for Study: NCT02511184 Crizotinib Plus Pembrolizumab in ALK-Positive Advanced Non Small Cell Lung Cancer Patients," Clinical Trials.gov, Archive, Sep. 25, 2015 (11 pages).

Boyerinas, et al., "Antibody-Dependent Cellular Cytotoxicity Activity of a Novel Anti-PD-L1 Antibody Avelumab (MSB0010718C) on Human Tumor Cells," Cancer Immunology Research, 3(10):1148-1157 (2015).

Brahmer et al., "Safety and activity of anti-PD-L1 antibody in patients with advanced cancer", The New England Journal of Medicine, 366:2455-2465 (2012).

Brown, et al., "Targeting DNA Repair in Cancer: Beyond PARP Inhibitors," Cancer Discovery 7(1):20-37 (2017).

Dong, et al., "B7-H1, a third member of the B7 family, co-stimulates T-cell proliferation and interleukin-10 secretion," Nature Medicine, 5(12):1365-9 (1999).

Fellouse, et al., "Synthetic antibodies from a four-amino-acid code: a dominant role for tyrosine in antigen recognition," PNAS, 101(34):12467-72 (2004).

Freeman, et al., "Engagement of the PD-1 inununoinhibitory receptor by a novel B7 family member leads to negative regulation of lymphocyte activation," Journal of Experimental Medicine, 192(7):1027-34 (2000).

Fury, et al., "Clinical Activity and Safety of Medi4736, An Anti-Pd-L1 Antibody, In Patients With Head and Neck Cancer", Annals of Oncology, 25(Suppl 4)iv340-iv365 (2014).

Gadiot, et al., "Overall survival and PD-L1 expression in metastasized malignant melanoma," Cancer 117(10):2192-201 (2011).

(56) References Cited

OTHER PUBLICATIONS

Goytisolo, et al., "The absence of the DNA-dependent protein kinase catalytic subunit in mice results in anaphase bridges and in increased telomeric fusions with normal telomere length and G-strand overhang," Molecular and Cellular Biology, 21(11):3642-51 (2001).
Higuchi, et al., "CTLA-4 Blockade Synergizes Therapeutically with PARP Inhibition in BRCA1-Deficient Ovarian Cancer," Cancer Immunology Research, 3(11):1257-68 (2015).
Higuchi, et al., "PARP inhibition synergizes with anti-CTLA-4 immune therapy to promote rejection of peritoneal tumors in mouse models of ovarian cancer," Gynecologic Oncology, 133:115-116(2014).
Horton et al., "Agonistic 4-1bb antibodies in combination with inhibitory antibodies against CTLA-4, PD-L1 or LAG-3 ACT or CD8+ T cells in the tumor microenvironment and synergize to promote regression of established tumors," Journal of Immunotherapy of Cancer, 2(Suppl 3):P213 (2014) (2 pages).
Hu-Lowe et al., "Nonclinical antiangiogenesis and antitumor activities of axitinib (AG-013736), an oral, potent, and selective inhibitor of vascular endothelial growth factor receptor tyrosine kinases 1, 2, 3," Clinical Cancer Research, 14(22):7272-7283 (2008).
Iwai, et al., "Involvement of PD-L1 on tumor cells in the escape from host immune system and tumor immunotherapy by PD-L1 blockade," PNAS, 99(19): 12293-7 (2002).
Keir, et al., "PD-1 and its ligands in tolerance and immunity," Annual Review of Immunology, 26:677-704 (2008).
Kelly, et al., "Avelumab (MSB00010718C; anti-PD-L1) in patients with advanced cancer: Safety data from 1300 patients enrolled in the phase 1b JAVELIN Solid Tumor Trial," Journal of Clinical Oncology, 343(15):3055 (4 pages) (2016).
Kohler, et al., "Continuous cultures of fused cells secreting antibody of predefined specificity," Nature, 256(5517):495-7 (1975).
Latchman, et al., "PD-L2 is a second ligand for PD-1 and inhibits T cell activation," Nature Immunology, 2(3):261-8 (2001).
Le, et al., Human antibodies for immunotherapy development generated via a human B cell hybridomatechnology, PNAS,103(10):3557-62 (2006).
Le, et al., "PD-1 Blockade in Tumors with Mismatch-Repair Deficiency," New England Journal of Medicine, 372(26):2509-20 (2015).
Liao et al., "Treating patients with ALK-positive non-small cell lung cancer: latest evidence and management strategy," Therapeutics Advances in Medical Oncology, 7(5):274-290 (2015).
Lutzky et al., "A Phase 1 study of MEDI4736, ananti-PD-L1 antibody, in patients with advanced solid tumors," Journal of Clinical Oncology; 2014 ASCO Annual Meeting, American Society of Clinical Oncology, 32(15 Suppl):3001 (2014) (1 page).
Morales-Kastresana et al., "Combined Immunostimulatory Monoclonal Antibodies Extend Survival in an Aggressive Transgenic Hepatocellular Carcinoma Mouse Model," Clinical Cancer Research; 19(22):6151-6162 (2013).
Okazaki, et al., "PD-1 and PD-1 ligands: from discovery to clinical application," International Immunology, 19(7):813-24 (2007).
Pal, et al., "Programmed death-1 inhibition in renal cell carcinoma: clinical insights and future directions," Clinical Advances in hematology and Oncology, 12(2):90-99 (2014).
Powles et al., "Inhibition of PD-L1 by MPDL3280A and clinical activity in pts with metastatic urothelial bladder cancer (UBC)," Journal of Clinical Oncology, 2014 ASCO Annual Meeting Abstracts, No. 15 (2014) (1 page).
Segal et al., "Preliminary data from a multi-arm expansion study of MEDI4736, an anti-PD-L1 antibody," Journal of Clinical Oncology, 32(15):Abstract (2014) (1 page).
Smith, et al., "The DNA-dependent protein kinase," Genes and Development, 13(8):916-34 (1999).
Taube, et al., "Colocalization of inflammatory response with B7-h1 expression in human melanocytic lesions supports an adaptive resistance mechamsm of immune escape," Science Translational Medicine, 4(127):127ra37 (2012).
Thompson, et al., "Costimulatory B7-H1 in renal cell carcinoma patients: Indicator of tumor aggressiveness and potential therapeutic target," PNAS 101(49):17174-9 (2004).
Thompson, et al., "Tumor B7-H1 is associated with poor prognosis in renal cell carcinoma patients with long-term follow-up," Cancer Research, 66(7):3381-5 (2006).
Topalian, et al., "Safety, activity, and immune correlates of anti-PD-1 antibody in cancer," New England Journal of Medicine, 366 (26):2443 (2012).
Williams et al., "Telomere dysfunction and DNA-PKcs deficiency: characterization and consequence," Cancer Research, 69(5):2100-7 (2009).
Amin, et al., "Nivolumab (anti-PD-1; BMS-936558, ONO-4538) in combination with sunitinib or pazopanib in patients (pts) with metastatic renal cell carcinoma (mRCC)," Journal of Clinical Oncology, 32(15):5010 (2014).
Gross-Goupil, et al., "Axitinib: a review of its safety and efficacy in the treatment of adults with advanced renal cell carcinoma," Clinical Medicine Insights: Oncology, 7:269-277 (2013).
Heery, et al., "Phase I open-label, multiple ascending dose trial of MSB0010718C, an anti-PD-L1 monoclonal antibody, in advanced solid malignancies," Journal of Clinical Oncology, 32(15):3064 (2014).
Powles et al., "MPDL3280A (anti-PD-L1) Treatment Leads to Clinical Activity in Metastatic Bladder Cancer," Nature, 515(7528):558-562 (2014).
Tanaka et al., "Anti-PD-1 Antibody: Basics and Clinical Application," Japanese Journal of Cancer and Chemotherapy, 40(9): 1145-1149 (2013).
Gulley, et al., "Exposure-response and PD-L1 expression analysis of second-line avelumab in patients with advanced NSCLC: Data from the JAVELIN Solid Tumor trial," Journal Of Clinical Oncology, 35(15 Supp):9086 (2017)(2 pages).
Heery, et al., "Avelumab for metastatic or locally advanced previously treated solid tumours (JAVELIN Solid Tumor): a phase la, multicohort, dose-escalation trial," Lancet Oncology, 18(5):587-598 (2017).
Passiglia, et al., "PD-L1 expression as predictive biomarker in patients with NSCLC: a pooled analysis," Oncotarget, 7(15):1973 8-19747 (2016).
Shitara, et al., "Phase I, open-label, multi-ascending dose trial of avelumab (MSB0010718C), an anti-PD-L1 monoclonal antibody, in Japanese patients with advanced solid tumors," Journal of Clinical Oncology, 22(15 Supp):3023 (2015) (2 pages).
Atkins et al., "Axitinib in Combination with Pembrolizumab in Patients with Advanced Renal Cell Carcinoma," presented at the European Society of Medical Oncology (ESM), Oct. 7-11, 2016, Copenhagen Denmark (1 page).
Atkins, et al., "Axitinib in Combination with Pembrolizumab in Patients with Advanced Renal Cell Cancer: a Non-Randomised, Open-Label, Dose-Finding, and Dose-Expansion Phase lb Trial," The Lancel Oncology, 19(3):405-415 (2018).
Bai, et al., "A Guide to Rational Dosing of Monoclonal Antibodies," Clinical Pharmacokinetics, 51(2):119-135 (2012).
Bailey, et al., "Immune Checkpoint Inhibitors as Novel Targets for Renal Cell Carcinoma Therapeutics," The Cancer Journal, 19(4):348-352 (2013).
Choueiri, et al., "Trial in Progress: Phase lb Dose-Finding Study of Axitinib Plus Pembrolizumab for First-Line Treatment of Advanced Renal Cell Carcinoma (RCC)," BJU International, 114(Supp. 4):4-5 (2014).
Clinical Trial NCT01472081, "Nivolumab (BMS-936558; MDX-1106) in Combination with Sunitinib, Pazopanib, or Ipilimumab in Subjects with Metastatic Renal Cell Carcinoma (RCC) (CheckMate 016)" (12 pages) (Study record version available online at clinicaltrials(dot)govict2/history/NCTO 1472081, submitted Jun. 12, 2019).
Clinical Trial NCT01472081, "Nivolumab (BMS-936558; MDX-1106) in Combination with Sunitinib, Pazopanib, or Ipilimumab in Subjects with Metastatic Renal Cell Carcinoma (RCC) (CheckMate 016)" (5 pages) (Study record version available online at clinicaltrials(dot)govict2/history/NCTO 1472081, submitted Jun. 12, 2019).

(56) References Cited

OTHER PUBLICATIONS

Clinical Trial NCT01984242, "A Study of Atezolizumab (an Engineered Anti-Programmed Death-Ligand 1 [PD-L1] Antibody) as Monotherapy or in Combination with Bevacizumab (Avastin®) Compared to Sunitinib (Sutent®) in Participants with Untreated Advanced Renal Cell Carcinoma (IMmotion150)" (5 pages) (Study record version available online at clinicaltrials(dot)govict2/history/NCT019 84242, submitted Jun. 12, 2019).
Clinical Trial NCT02036502, "A study of Pembrolizumab (MK-3475) in Combination with Standard of Care Treatments in Participants with Multiple Myeloma (MK-3475-023/KEYNOTE-023)" (11 pages) (Study record version available online at ClinicalTrials(dot)gov archive, submitted Apr. 24, 2018).
Clinical Trial NCT02036502, "A study of Pembrolizumab (MK-3475) in Combination with Standard of Care Treatments in Participants with Multiple Myeloma (MK-3475-023/KEYNOTE-023)" (5 pages) (Study record version available online at clinicaltrials(dot)gov/ct2/history/NCT02036502, submitted Apr. 24, 2018).
Clinical Trial NCT02039674, "A Study of Pembrolizumab (MK-3475) in Combination with Chemotherapy or Immunotherapy in Participants with Non-Small Cell Lung Cancer (MK-3475-021/KEYNOTE-021)" (5 pages) (Study record version available online at clinicaltrials(dot)govict2/history/NCT02039674, submitted Jun. 12, 2019).
Clinical Trial NCT02039674, "A Study of Pembrolizumab (MK-3475) in Combination with Chemotherapy or Immunotherapy in Participants with Non-Small Cell Lung Cancer (MK-3475-021/KEYNOTE-021)," (6 pages) (Study record version available online at clinicaltrials(dot)govict2/history/NCT02039674, submitted Jan. 11, 2019).
Clinical Trial NCT02133742, "A Dose Finding Study to Evaluate Safety, Drug Interaction, Tumor Markers of Axitinib in Combination with MK-3475 in Adult Patients with Previously Untreated Advanced Renal Cell Cancer" (1 page) (Study record version available online at clinicaltrials(dot)govict2/history/NCT02133742, submitted Jun. 20, 2019).
Clinical Trial NCT02133742, "A Dose Finding Study to Evaluate Safety, Drug Interaction, Tumor Markers of Axitinib in Combination with MK-3475 in Adult Patients with Previously Untreated Advanced Renal Cell Cancer" (8 pages) (Study record version available online at clinicaltrials(dot)govict2/history/NCT02133742, submitted Jun. 20, 2019).
Clinical Trial NCT02133742, "A Phase 1 B, Open Label, Dose Finding Study To Evaluate Safety, Pharmacokinetics and Pharmacodynamics of Axitinib (AG-013736) In Combination With MK-34 75 In Patients With Advanced Renal Cell Cancer," ClinicalTrials.gov archive, (May 7, 2014), Retrieved from the Internet: URL:https//clinicaltrials.govjarchive/NCT 02133742/2014 05 07 [retrieved on-Mar. 30, 2015] (3 pages).
Clinical Trial NCT02179918, "APhase 1 Study of the 4-IB Agonsit PF-05082566 in Combination with the PD-1 Inhibitor MK-3475 in Patients with Advanced Solidy Tumors," Clinical Trials.gov (Jul. 1, 2014), pp. 1-6. Retrieved from the Internet URL: https://clmicaltrials.gov/archive/NCT02179918/2014 07 01 (6 pages).
Clinical Trial NCT02331368, "Phase 2 Multi-Center Study of Anti-PD-1 during Lymphopenic State after HDT/ASCT for Multiple Myeloma" (4 pages) (Study record version available online at clinicaltrials(dot)govict2/history/NCT02331368, submitted Jul. 2, 2018).
Clinical Trial NTC02014636, "Safety and Efficacy Study of Pazopanib and MK 3475 in Advanced Renal Cell Carcinoma (RCC; KEYNOTE-018)" (6 pages) (Study record version available online at https//clinicaltrials(dot)gov/ct2/history/NCT02014636, submitted Apr. 26, 2019).
Clinical Trials: NCT02014636, "A Phase I/II Study to Assess the Safety and Efficacy of Pazopanib and MK 34 75 in Subjects With Advanced Renal Cell Carcinoma," Clinical Trials.gov (Jan. 24, 2014), pp. 1-11. Retrieved from the Internet URL: https//clinicaltrials.gov/archive/NCT02014636/2014 01 24 [retrieved on Mar. 31, 2015] (11 pages).

Czarnecka, et al., "The Activity of Tyrosine Kinase Inhibitors on Clear Cell Renal Cell Carcinoma Tumor Initiating Cells in Hypoxic Microenvironment," BJUI Supplements, The 11th International Kidney Cancer Symposium Annual Meeting Proceedings, 110(Suppl. 2):1-20 (2012).
Dorff, et al., "Novel Tyrosine Kinase Inhibitors for Renal Cell Carcinoma," Expert Review of Clinical Pharmacology, 7(1):67-73 (2014).
Domblides, et al., "Emerging Antiangiogenics for Renal Cancer," Expert Opinion on Emerging Drugs, 18(4):495-511 (2013) (published online Dec. 2, 2013).
Dong et al., "Tumor-associated B7-H1 promotes T-cell apoptosis: a potential mechanism of immune evasion," Nature Medicine, 8(8):793-800 (2002).
Duraiswamy, et al., "Therapeutic PD-1 pathway blockade augments with other modalities of immunotherapy T-cell function to prevent immune decline in ovarian cancer," Cancer Research, 73(23):6900-6912 (2013).
Escudier, et al., "Axtinib for the management of metastatic renal cell carcinoma," Drugs in R&D 11(2):113-126 (2011).
Escudier, et al., "Optimal Management of Metastatic Renal Cell Carcinoma: Current Status," Drugs, 73:427-438 (2013).
European Search Report in European Application No. 18205542, dated Mar. 21, 2019 (8 pages).
FDA-Approved Patient Labeling for INLYTA, referenceID:3078397 (Jan. 2012) (22 pages).
Gao et al., "Overexpression of PD-L1 significantly associates with tumor aggressiveness and postoperative recurrence in human hepatocellular carcinoma," Clinical Cancer Research, 15(3):971-979 (2009).
Ghebeh et al., "FOXP3+ Tregs and B7-H1+/PD-1+ T lymphocytes co-infiltrate the tumor tissues of high-risk breast cancer patients: Implication for inununotherapy," BMC Cancer, 8:57 (12 pages) (2008).
Ghebeh et al., "The B7-H1 (PD-L1) T lymphocyte-inhibitory molecule is expressed in breast cancer patients with infiltrating ductal carcinoma: correlation with important high-risk prognostic factors," Neoplasia, 8(3): 190-198 (2006).
Hamanishi et al., "Programmed cell death 1 ligand 1 and tumor-infiltrating CD8+ T lymphocytes are prognostic factors of human ovarian cancer," Proceeding of the National Academy of Sciences, 104(9):3360-3365 (2007).
Hamid et al., "Safety and tumor responses with lambrolizumab (anti-PD-1) in melanoma," New England Journal of Medicine, 369(2):134-144 (2013).
Hino et al., "Tumor cell expression of programmed cell death-1 ligand 1 is a prognostic factor for malignant melanoma," Cancer, 116(7):1757-1766 (2010).
Inman et al., "PD-L1 (B7-H1) expression by urothelial carcinoma of the bladder and BCG-induced granulomata: associations with localized stage progression," Cancer, 109(8):1499-1505 (2007).
Joshi, "ASCO GU 2018: Safety and Efficacy of Axitinib in Combination with Pembrolizumab in Patients with Advanced Renal Cell Cancer" available at www.urotoday.com (downloaded Oct. 19, 2018) (2 page).
Kaufman, et al., "The Society for Immunotherapy of Cancer Consensus Statement on Tumour Immunotherapy for the Treatment of Cutaneous Melanoma," Nature, 10:588-598 (2013).
Lipson, et al., "Durable Cancer Regression Off-Treatment and Effective Reinduction Therapy withan Anti-PD-1 Antibody," Clinical Cancer Research, 19:462-468 (2013).
Massari, et al., "PD-1 Blockade Therapy in Renal Cell Carcinoma: Current Studies and Future Promises," Cancer Treatment Reviews, 41:114-121 (2015).
McDermott et al., "PD-1 as a potential target in cancer therapy," Cancer Medicine, 2(5):662673 (2013).
Nakanishi et al., "Overexpression of B7-H1 (PD-L1) significantly associates with tumor grade and postoperative prognosis in human urothelial cancers," Cancer Immunology, Immunotherapy, 56(8):1173-1182 (2007).
Nomi et al., "Clinical significance and therapeutic potential of the programmed death-1 ligand/programmed death-1 pathway in human pancreatic cancer," Clinical Cancer Research, 13(7):2151-2157 (2007).

(56) References Cited

OTHER PUBLICATIONS

Ohigashi et al., "Clinical significance of programmed death-1 ligand-1 and programmed death-1 ligand-2 expression in human esophageal cancer," Clinical Cancer Research, 11(8):2947-2953 (2005).
Pal, et al., "Novel Therapies for Metastatic Renal Cell Carcinoma: Efforts to Expand beyond the VEGF/mTOR Signaling Paradigm," Molecular Cancer Therapeutics, 11(3):526-537 (2012).
Pardoll, "The Blockade of Immune Checkpoints in Cancer Immunotherapy," Nature, 12:252-264 (2016).
Patel, et al., "Clinical Cancer Advances 2013: Annual Report on Progress Against Cancer from the American Society of Clinical Oncology," Journal of Clinical Oncology, 32(2):129-160 (2014) (published online Dec. 10, 2013).
Patnaik et al., "Phase I Study of MK-3475 (Anti-PD-1 Monoclonal Antibody) in Patients with Advanced Solid Tumors," Journal of Clinical Oncology., 30(Supp.15):2512 (2012) (2 pages).
Patnaik et al., "Phase I Study of Pembrolizumab (MK-3475; Anti-PD-1 Monoclonal Antibody) in Patients with Advanced Solid Tumors," Clinical Cancer Research; 21(19) (2015).
PCT International Search Report, International Application No. PCT/US2015/014212, dated Apr. 10, 2015 (12 pages).
Procopio, et al., "Combination Therapies for Patients with Metastatic Renal Cell Carcinoma," Lancet, 19:281-283 (2018).
Rini, et al., "Five-Year Survival in Patients with Cytokine-Refractory Metastatic Renal Cell Carcinoma Treated with Axitinib," Clinical Genitourinary Cancer, 11(2):107-114 (2013).
Rini, et al., "Pembrolizumab Plus Axitinib Versus Sunitinib for Advanced Renal-Cell Carcinoma," The New England Journal of Medicine, 380:1116-1127 (2019).
Robert, et al., "Drug of the Year: Programmed Death-1 Receptor/Programmed Death-1 Ligand-1 Receptor Monoclonal Antibodies," European Journal of Cancer, 49:2968-2971 (2013).
Robert, et al., "LBA34-Pembrolizumab (Pembro:MK-3475) for Advanced Melanoma (MEL): Randomized Comparison of Two Dosing Schedules," Annals of Oncology, 25(Suppl.4):1-41 (Sep. 2014).
Rothermundt, et al., "Successful treatment with an anti-PD-1 antibody for progressing brain metastases in renal cell cancer," Annals of Oncology, 25:544- 552 (2016).
Seliger, et al., "Abstracts from the 25th Annual Scientific Meeting of the International Society for Biological Therapy of Cancer (now the Society of Immunotherapy of Cancer)", Journal of Immunotherapy, 34(2):221-227 (2011).
Sequence Listing from International Application No. PCT/US2008/007463, filed Jun. 13, 2008 (24 pages).
Sharpe, et al., "The function of programmed cell death 1 and its ligands in regulating autoimmunity and infection," Nature Immunology, 8(3):239-245 (2007).
Shimauchi, et al., "Augmented expression of programmed death-1 in both neoplastic and non-neoplastic CD4+ T-cells in adult T-cell leukemia/lymphoma," International Journal of Cancer, 121(12):2585-2590 (2007).
Sliwkowski, et al., "Antibody Therapeutics in Cancer," Science, 341:1192-1198 (2013).
Solowiej, et al., "Characterizing the effects of the juxtamembrane domain on vascular endothelial growth factor receptor-2 enzymatic activity, autophosphorylation, and inhibition by axitinib," Biochemistry, 48(29):7019-31 (2009).
Stehle, et al., "Reduced Immunosuppressive Properties of Axitimb in Comparison with OtherTyrosine Kinase Inhibitors," J. Biol. Chem., 288(23):16334-16347 (2013).
Sznol, et al., "Phase lb evaluation of MPDL3280A (anti-PDFL1) in connection with bevacizumab (bev) in patients (pts) with metastic renal cell carcinoma (mRCC)," Journal of Clinical Oncology, 33(7): Abstract (2015) (3 pages).
Taiwan Search Report for Application No. CN104103603, dated Sep. 11, 2018 (14 pages).
Tang, et al., "Programmed Death 1 Pathway Inhibition in Metastatic Renal Cell Cancer and Prostate Cancer," Current Oncology Reports, 15:98-104 (2013).
Thompson, et al., "PD-1 is expressed by tumor-infiltrating immune cells and is associated with poor outcome for patients with renal cell carcinoma," Clinical Cancer Research, 13(6):1757 1761(2007).
Thompson, et al., "Significance of B7-H1 overexpressioninkidney cancer," Clinical Genitourin Cancer, 5(3):206-211 (2006).
Tykodi, "Progress and Potential of Immune Checkpoint Blockage for Treating Advanced Renal Cell Carcinoma," Immunotherapy, 5(6):607-619 (2013).
Van Geel, et al.," Concise Drug Review: Pazopanib and Axitinib," The Oncologist, 17:1081-1089 (2012).
Wei, et al., "Combinatorial PD-1 blockade and CD137 activation has therapeutic efficacy in murine cancer models and synergizes with cisplatin," PLOS One, 8(12):e84927 (11 pages) (2013).
WHO Drug Information, vol. 27, No. 2, pp. 161-162 (2013).
Yang, et al., "PD-L1: PD-1 interaction contributes to the functional suppression of T-cell responses to human uveal melanoma cells in vitro," Investigative Ophthalmology & Visusal Science, 49(6):2518-2525 (2008.
Yasuda et al., "Simultaneous blockade of programmed death 1 and vascular endothelial growth factor receptor 2 (VEGFR2) induces synergistic anti-tumour effect in vivo," Clinical and Experimental Immunology, 172(3):500-506 (2013).
Yousaf, et al., "Axitinib in advanced renal-cell carcinoma," The Lancet Oncology, 12(13):1245-1246 (2013).
Gulley et al., "Avelumab (MSB0010718C), an anti-PD-L1 antibody, in advanced NSCLC patients: A phase lb, open-label expansion trial in patients progressing after platinum-based chemotherapy," Journal of Clinical Oncology, 33(15):8034 (2015) (4 pages).
Wang et al., "Fixed dosing versus body size-based dosing of monoclonal antibodies in adult clinical trials," Journal of Clinical Pharmacology, 49:1012-1024 (2009).

* cited by examiner

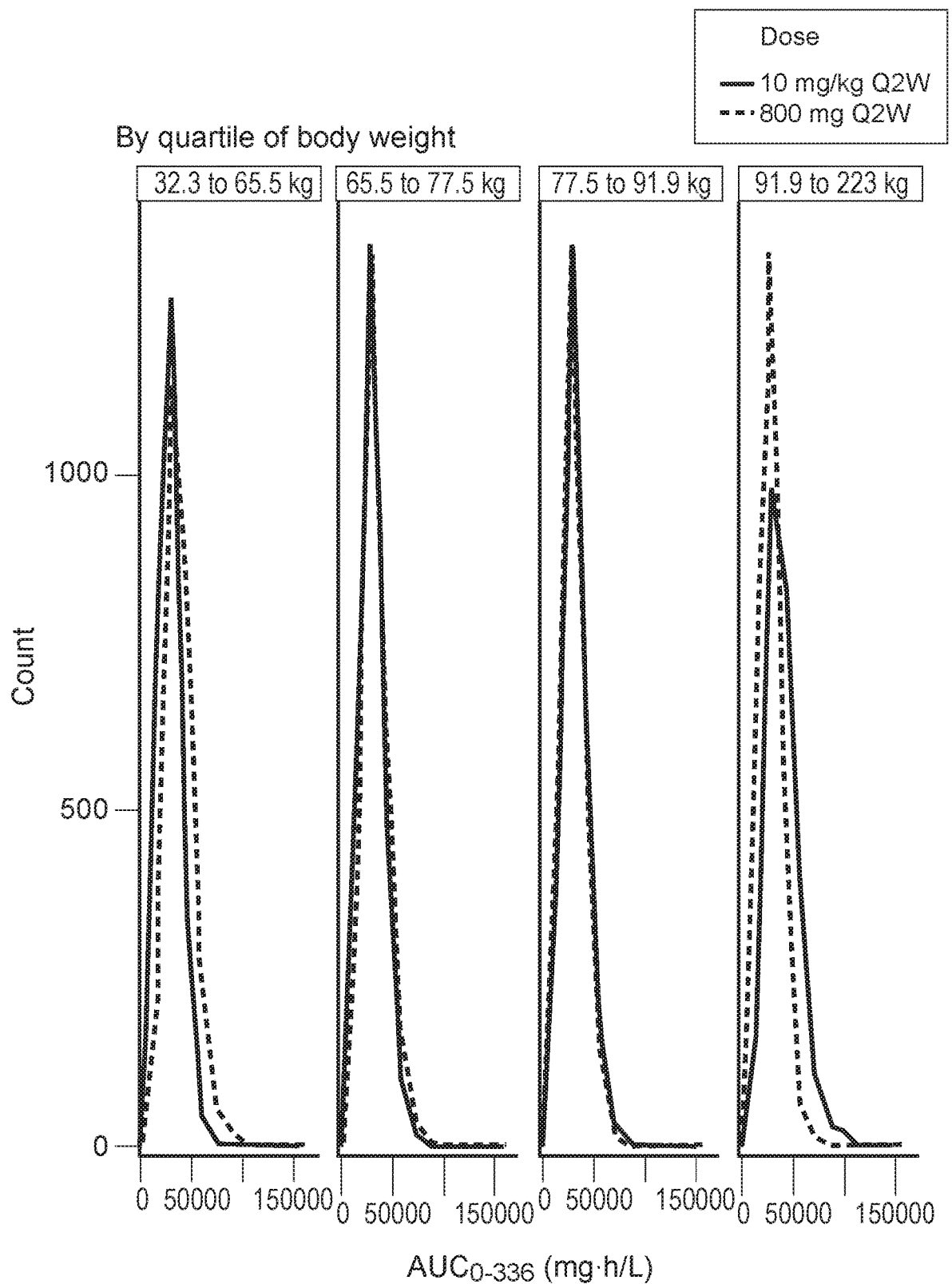

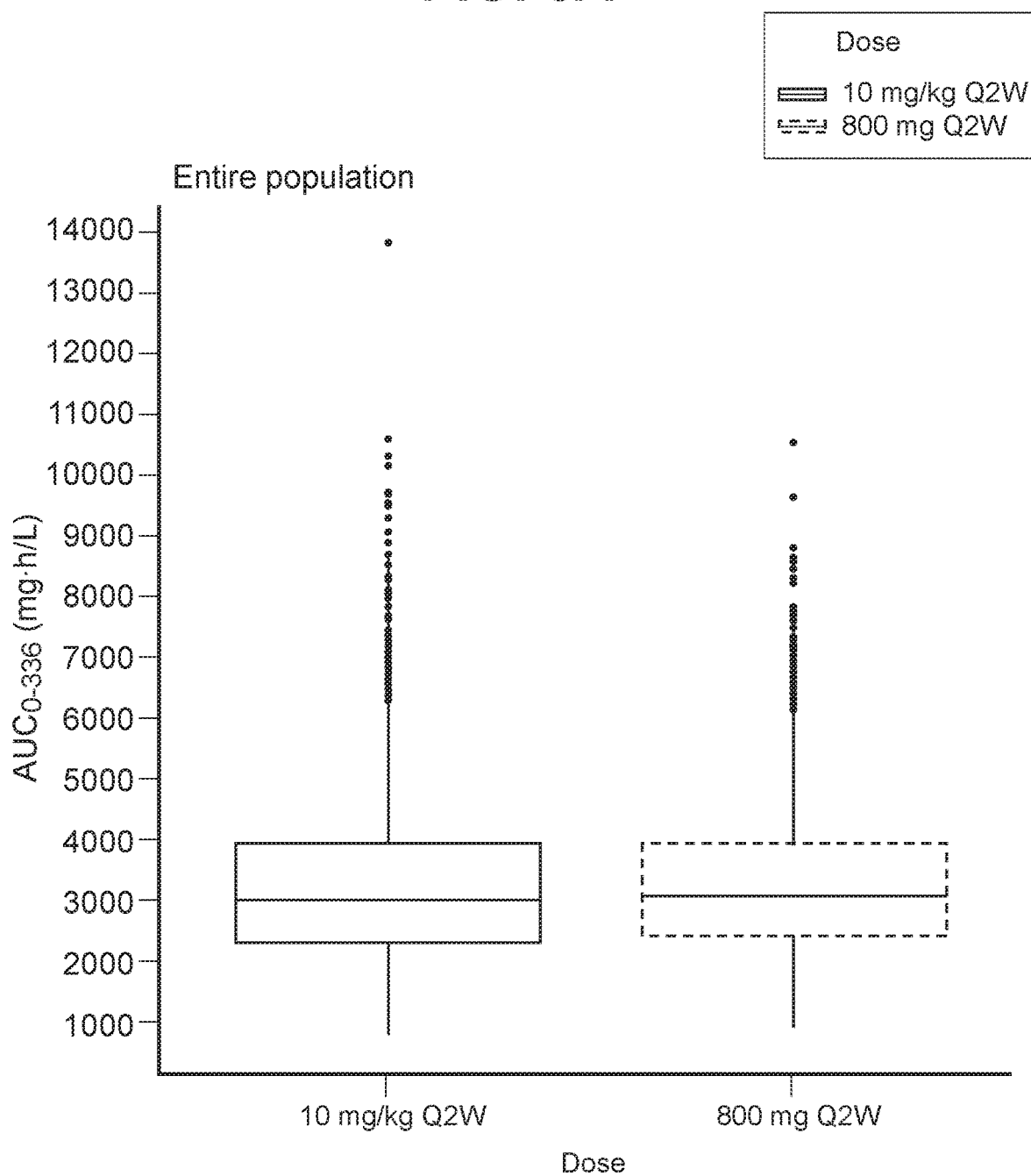

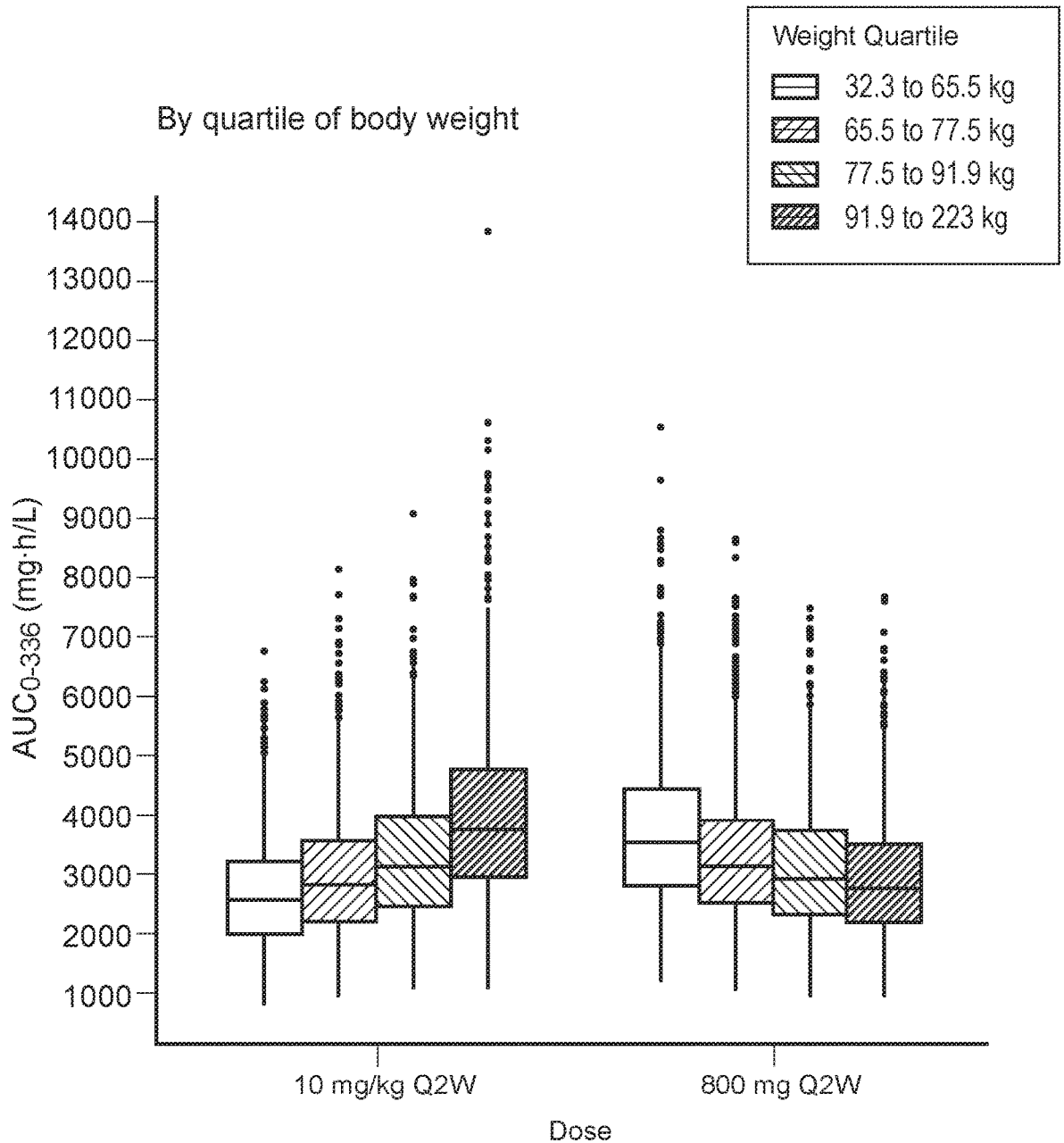

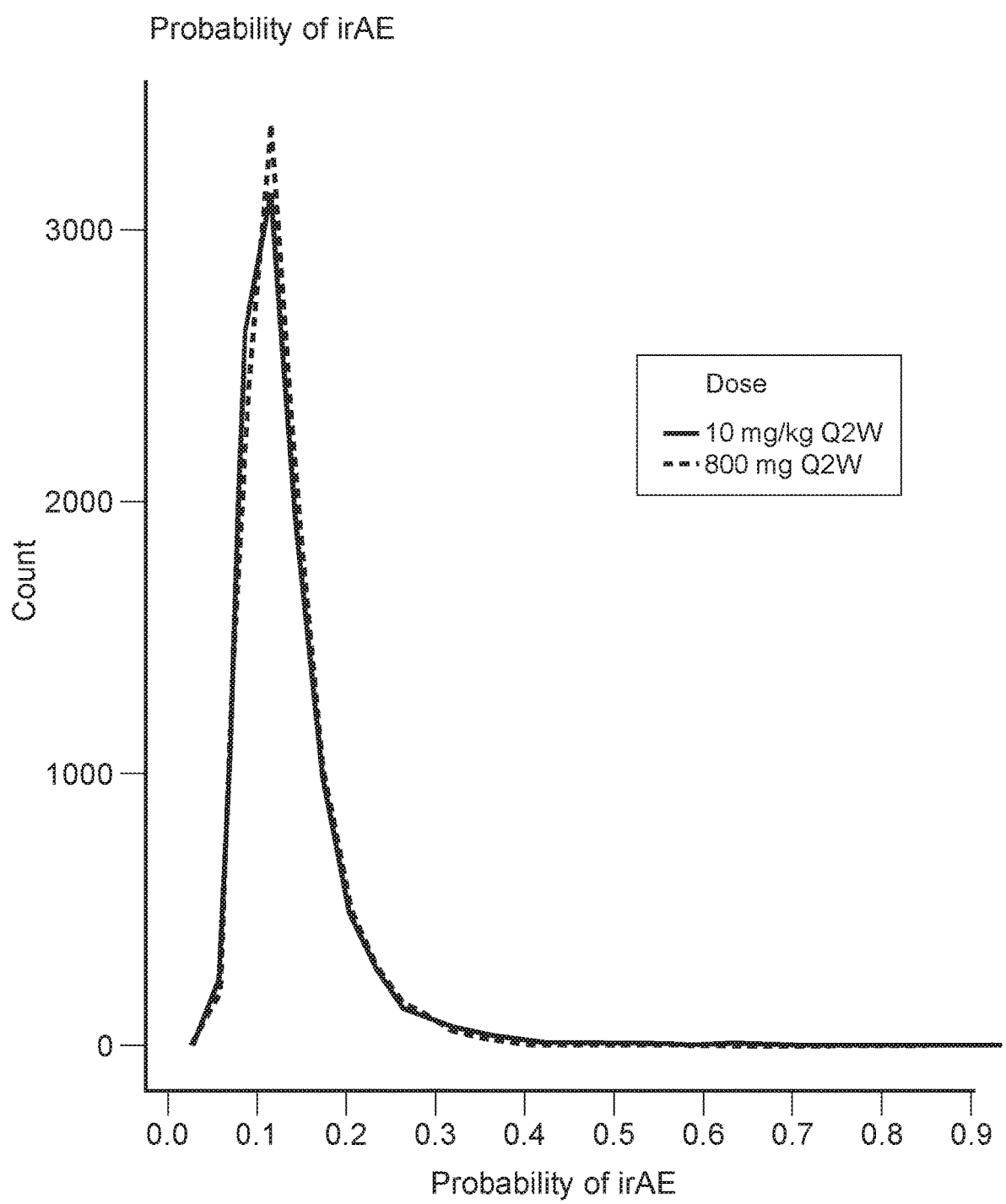

DOSING REGIMEN OF AVELUMAB FOR THE TREATMENT OF CANCER

FIELD

The present invention relates to dosing regimens of avelumab for the treatment of cancer. In particular, the invention relates to improved dosing regimens of avelumab for the treatment of cancer.

BACKGROUND

The programmed death 1 (PD-1) receptor and PD-1 ligands 1 and 2 (PD-L1 and PD-L2, respectively) play integral roles in immune regulation. Expressed on activated T25 cells, PD-1 is activated by PD-L1 (also known as B7-H1) and PD-L2 expressed by stromal cells, tumor cells, or both, initiating T-cell death and localized immune suppression (Dong et al., Nat Med 1999; 5:1365-69; Freeman et al. J Exp Med 2000; 192:1027-34), potentially providing an immune-tolerant environment for tumor development and growth. Conversely, inhibition of this interaction can enhance local T30 cell responses and mediate antitumor activity in nonclinical animal models (Iwai Y, et al. Proc Natl Acad Sci USA 2002; 99:12293-97).

Avelumab is a fully human mAb of the IgG1 isotype that specifically targets and blocks PD-L1. Avelumab is the International Nonproprietary Name (INN) for the anti-PD-L1 monoclonal antibody MSB0010718C and has been described by its full length heavy and light chain sequences in WO2013079174, where it is referred to as A09-246-2. The glycosylation and truncation of the C-terminal Lysine in its heavy chain is described in WO2017097407. Avelumab has been in clinical development for the treatment of Merkel Cell Carcinoma (MCC), non-small cell lung cancer (NSCLC), urothelial carcinoma (UC), renal cell carcinoma (RCC) and a number of other cancer conditions of a dosing regimen of 10 mg/kg Q2W.

SUMMARY OF THE INVENTION

This invention relates to dosing regimens of avelumab for the treatment of cancer. More specifically, the invention relates method of treating cancer in a patient, comprising administering to the patient a dosing regimen that provides a higher mean exposure, as measured by $C_{trough}$ or other suitable PK parameters, of avelumab in the patient, than the current dosing regimen of 10 mg/kg Q2W that are used in the clinical trials.

In one embodiment, the invention relates to a method of treating a cancer in a patient, comprising administering avelumab to the patient in a dosing regimen of 5-10 mg/Kg Q1W. In one aspect of this embodiment, the dosing regimen is 5 mg/kg Q1W, 6 mg/kg Q1W, 7 mg/kg Q1W, 8 mg/kg Q1W, 9 mg/kg Q1W or 10 mg/kg Q1W. More preferably, the dosing regimen is 5 mg/kg Q1W, 8 mg/kg Q1W or 10 mg/kg Q1W. Even more preferably, the dosing regimen is 10 mg/kg Q1W. In another aspect of this embodiment, and in combination with any other aspects of this embodiment, the cancer is selected from the group consisting of MCC, NSCLC, RCC, bladder cancer, ovarian cancer, head and neck cancer, gastric cancer, mesothelioma, urothelial carcinoma, breast cancer, adenocarcinoma of the stomach and thymoma. Preferably, the cancer is MCC, NSCLC, RCC, bladder cancer, ovarian cancer, head and neck cancer and gastric cancer. More preferably, the cancer is MSCLC or MCC. In another embodiment, the invention relates to a method of treating a cancer in a patient, comprising administering avelumab to the patient in a dosing regimen of 11-20 mg/kg Q2W. In one aspect of this embodiment, the dosing regimen is 11, 12, 13, 14, 15, 16, 17, 18, 19 or 20 mg/kg Q2W. Preferably, the dosing regimen is 13, 15, 17 or 20 mg/kg Q2W. More preferably, the dosing regimen is 15 or 20 mg/kg Q2W. Even more preferably, the dosing regimen is 20 mg/kg Q2W. In another aspect of this embodiment, and in combination with any other aspects of this embodiment, the cancer is selected from the group consisting of MCC, NSCLC, RCC, bladder cancer, ovarian cancer, head and neck cancer gastric cancer, mesothelioma, urothelial carcinoma, breast cancer, adenocarcinoma of the stomach and thymoma. Preferably, the cancer is MCC, NSCLC, RCC, bladder cancer, ovarian cancer, head and neck cancer gastric cancer. More preferably, the cancer is MSCLC or MCC.

In another embodiment, the invention relates to a method of treating a cancer in a patient, comprising administering avelumab to the patient in a dosing regimen of 15-30 mg/kg Q3W. In one aspect of this embodiment, the dosing regimen is, 15, 16, 17, 18, 19, 20, 21, 22, 23, 24, 25, 26, 27, 28 29 or 30 mg/kg Q3W. Preferably, the dosing regimen is 15, 20, 25 or 30 mg/kg Q3W. More preferably, the dosing regimen is 15, 20 or 25 mg/kg Q3W. Even more preferably, the dosing regimen is 20 mg/kg Q3W. In another aspect of this embodiment, and in combination with any other aspects of this embodiment, the cancer is selected from the group consisting of MCC, NSCLC, RCC, bladder cancer, ovarian cancer, head and neck cancer gastric cancer, mesothelioma, urothelial carcinoma, breast cancer, adenocarcinoma of the stomach and thymoma. Preferably, the cancer is MCC, NSCLC, RCC, bladder cancer, ovarian cancer, head and neck cancer gastric cancer. More preferably, the cancer is MSCLC or MCC.

In another embodiment, the invention relates to a method of treating a cancer in a patient, comprising administering avelumab to the patient in a dosing regimen of X mg/kg Q1W for n weeks followed by Y mg/kg Q2W, wherein X is 5-20, Y is 10-20, n is 6, 12 or 18. In one aspect of this embodiment, n is 12. In another aspect of the embodiment, n is 6. In another aspect of the embodiment, and in combination with any other aspect of this embodiment, X is 5, 6, 7, 8, 9, 10, 11, 12, 13, 14, 15, 16, 19, 18, 19 or 20. Preferably, X is 5, 10, 15 or 20. More preferably, X is 5, 10, or 15. Even more preferably, X is 10. In another aspect of the embodiment, and in combination with any other aspect of this embodiment, Y is 10, 11, 12, 13, 14, 15, 16, 17, 18, 19 or 20. Preferably, Y is 10, 15 or 20. More preferably, Y is 10. In another aspect of this embodiment, and in combination with any other aspects of this embodiment, the cancer is selected from the group consisting of MCC, NSCLC, RCC, bladder cancer, ovarian cancer, head and neck cancer gastric cancer, mesothelioma, urothelial carcinoma, breast cancer, adenocarcinoma of the stomach and thymoma. Preferably, the cancer is MCC, NSCLC, RCC, bladder cancer, ovarian cancer, head and neck cancer gastric cancer. More preferably, the cancer is MSCLC or MCC.

In some embodiments, a flat dose can be used in place of the mg/kg dose mentioned above. Correlation between mg/kg dose and the flat dose can be made, e.g., as follows: 5 mg/kg is about 500 mg flat dose; 10 mg/kg is about 800 mg; 11 mg/mg is about 900 mg; 15 mg/kg is about 1240 mg flat dose; 20 mg is about 1600 mg flat dose and 30 mg/kg is about 2400 mg flat dose. Therefore, in another embodiment of the invention, the aforementioned embodiments based on a mg/kg dosing regimen of avelumab can be replaced with the corresponding flat dosing regimen as described herein.

In other embodiments, the invention relates to a method of treating a cancer in a patient, comprising administering avelumab to the patient a flat dosing regimen of avelumab. In one aspect of the embodiment, the flat dosing regimen is 400-800 mg flat dose Q1W. Preferably, the flat dosing regimen is 400 mg, 450 mg, 500 mg, 550 mg, 600 mg, 650 mg, 700 mg, 750 mg or 800 mg flat dose Q1W. Preferably, the flat dosing regimen is 800 mg flat dose Q1W. In another aspect of this embodiment, the flat dosing regimen is 880-1600 mg flat dose Q2W. Preferably the flat dosing regimen is 880 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg or 1600 mg flat dose Q2W. More preferably, the flat dosing regimen is 1200 mg or 1600 mg flat dose Q2W. In another aspect of this embodiment, the flat dosing regimen is 1200-2400 mg flat dose Q3W, preferably 1200 mg Q3W. Preferably, the flat dosing regimen is 1200 mg, 1250 mg, 1300 mg, 1350 mg, 1400 mg, 1450 mg 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg or 2400 mg flat dose Q3W. More preferably, the dosing regimen is 1200 mg flat dose Q3W. In another aspect of the embodiment, the flat dosing regimen is 400-1600 mg Q1W for n weeks followed by 800-1600 mg Q2W, wherein n is 6, 12 or 18. Preferably, the flat dosing regimen is 400 mg, 450 mg, 500 mg, 550 mg, 600 mg, 650 mg, 700 mg, 725 mg, 750 mg, 775 mg, 800 mg, 825 mg, 850 mg, 875 mg, 900 mg, 925 mg, 950 mg, 975 mg, 1000 mg, 1050 mg, 1100 mg, 1150 mg, 1200 mg, 1250 mg, 1300 mg, 1350 mg, 1400 mg, 1450 mg, 1500 mg, 1550 mg or 1600 mg Q1W for n weeks followed by 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg or 1600 mg Q2W. More preferably, the dosing regimen is 800 mg flat dose Q1W for n weeks followed by 800 mg flat dose Q2W. Even more preferably, n is 12. In another aspect of this embodiment, the flat dosing regimen is 400-800 mg flat dose Q2W. Preferably, the flat dosing regimen is 400 mg, 450 mg, 500 mg, 550 mg, 600 mg, 650 mg, 700 mg 750 mg or 800 mg flat dose Q2W. More preferably, the flat dosing regimen is 800 mg flat dose Q2W. In another aspect of this embodiment, and in combination with any other aspects of this embodiment not inconsistent, the cancer is selected from the group consisting of MCC, NSCLC, RCC, bladder cancer, ovarian cancer, head and neck cancer, gastric cancer, mesothelioma, urothelial carcinoma, breast cancer, adenocarcinoma of the stomach and thymoma. Preferably, the cancer is MCC, NSCLC, RCC, bladder cancer, ovarian cancer, head and neck cancer gastric cancer. More preferably, the cancer is NSCLC or MCC.

In another embodiment, the invention is directed to a method of treating a cancer comprising administering to the patient avelumab in a dosing regimen as described in any of the proceeding embodiments, wherein the patient has a TPS of PD-L1 expression of 1% and above, 5% and above, 10% and above, 20% and above, 30% and above, 40% and above, 50% and above, 60% and above, 70% and above, 80% and above 95% and above, or 95% and above. Preferably, the TPS of PD-L1 expression is 20% and above. More preferably, the TPS of PD-L1 expression is 50% and above.

In another embodiment, the invention is directed to a method of treating a cancer in a patient, comprising administering avelumab to the patient in a dosing regimen selected from the group consisting of 800 mg Q1W for 12 weeks followed by 800 mg Q2W, 10 mg/kg Q1W for 12 weeks followed by 10 mg/kg Q2W and 1200 mg Q3W, and wherein the tumor proportion score of PD-L1 expression is 5% and above, 20% and above, 50% and above or 80% and above. Preferably, tumor proportion score of PD-L1 expression is 20% and above. More preferably, the TPS of PD-L1 expression is 50% and above. In one aspect of this embodiment and the cancer is selected from NSCLC, urothelial cancer, RCC, ovarian cancer, head and neck cancer gastric cancer. More preferably, the cancer is NSCLC.

In another embodiment, the invention is directed to a method of treating a cancer comprising administering to the patient avelumab in a dosing regimen as described in any of the proceeding embodiments, further comprising administering to the patient at least one of a second anti-cancer treatment. In an aspect of this embodiment, the method further comprising administering one or two of a second anti-cancer treatment. Preferably, the second anti-cancer treatment is selected from the group consisting of a VEGFR antagonist, an anti-4-1BB antibody an anti-OX-40 antibody, an anti-MCSF antibody, an anti-PTK-7 antibody based antibody drug conjugate (ADC) wherein the drug payload is an antineoplastic agent, an IDO1 antagonist, an ALK antagonist, an anti-cancer vaccine, a radio therapy and a standard of care treatment of cancers of the relevant tumor type. Preferably, the VEGFR antagonist is axitinib, the anti-4-1BB antibody is PF0582566, the antiOX-40 antibody is PF4518600, the anti-MCSF antibody is PF-0360324, the ALK antagonist is crizotinib or lorlatinib (PF-06463922) and the anti-PTK7 antibody based ADC is PF-06647020.

BRIEF DESCRIPTION OF THE FIGURES AND DRAWINGS

FIG. 1 depicts the $C_{trough}$ v. ORR curve of 88 patients in phase III MCC trial.

FIG. 2. depicts the $C_{trough}$ v. ORR curve of 156 patients in phase III first line NSCLC patients FIG. 3 depicts the $C_{trough}$ v. ORR curve of 184 patients in phase I, $2^{nd}$ line NSCLC patients.

FIG. 4A and FIG. 4B depict the density plots showing the distribution of $AUC_{0-336h}$ (μgh/mL) after 10 mg/kg Q2W and flat 800 mg Q2W dosing using the PK SS model for the entire population (FIG. 4A) and split by quartiles of weight (FIG. 4B)

FIG. 5A and FIG. 5B depict the box and whisker plots showing the $AUC_{0-336h}$ (μgh/mL) after 10 mg/kg Q2W and 800 mg Q2W dosing using the PK SS model for the entire population (FIG. 5A) and split by quartiles of weight (FIG. 5B)

FIG. 9A and FIG. 9B depict the density plot (FIG. 9A) and box and whisker plot (FIG. 9B), using the PK SS model, showing the probably of experiencing an irAE after 10 mg/kg Q2W and 800 mg Q2W dose.

DETAILED DESCRIPTION OF THE INVENTION

Figure 1:
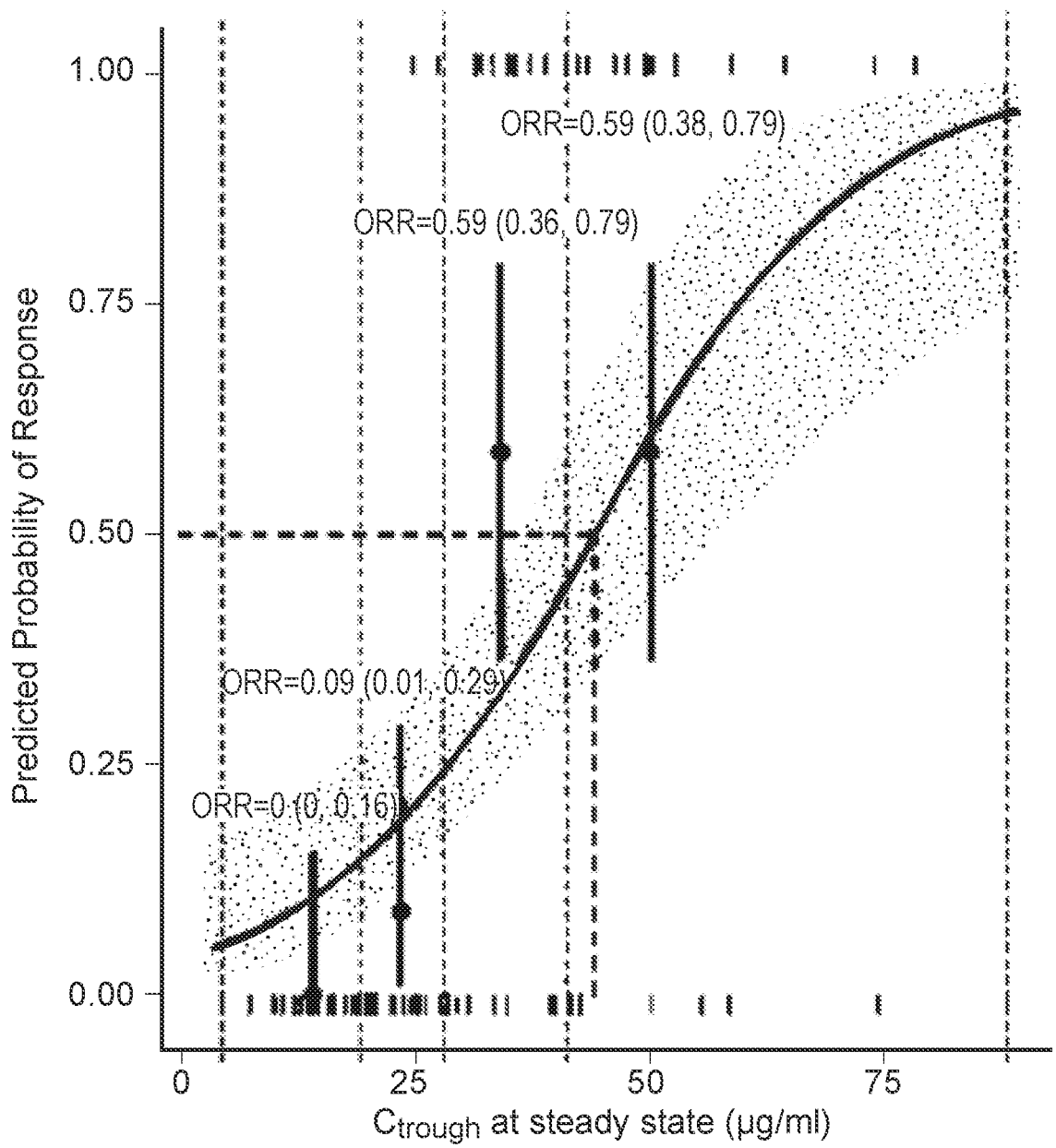

As used herein, the terms such as "area under curve" (AUC), $C_{trough}$, $C_{max}$, "best overall response" (BOR), "overall response rate" (ORR), Q1W, Q2W, Q3W have the meaning as they are generally known by one of the ordinary skill in the art.

As used herein, the term "anti-cancer treatment" refers to any standard of care treatment of cancers in any relevant tumor types, or the administration of any single pharmaceutical agent, any fixed dose combinations of two or more single pharmaceutical agents, other than the standard of care treatment of cancer, documented in the state of the art as having or potentially having an effect toward the treatment of cancer or in the relevant tumor types.

As used herein the term "standard of care treatment of cancers" refers to any non-surgical treatment of any particular tumor type that is suggested in the NCCN Guidelines Version 1 2017. For clarity, such standard of care treatment of cancers may be radiation or, the administration of a single pharmaceutical agent, a fixed dose combinations of two or more single pharmaceutical agents or the combination of two or more single pharmaceutical agents, provided that standard of care treatment of cancers does not already contain any PD-1 or PD-L1 antagonist.

As used herein the term "single pharmaceutical agent" means any composition that comprising a single substance as the only active pharmaceutical ingredient in the composition.

As used herein, the term "tumor proportion score" or "TPS" as used herein refers to the percentage of viable tumor cells showing partial or complete membrane staining in an immunohistochemistry test of a sample. "Tumor proportion score of PD-L1 expression" used here in refers to the percentage of viable tumor cells showing partial or complete membrane staining in a PD-L1 expression immunohistochemistry test of a sample. Exemplary samples include, without limitation, a biological sample, a tissue sample, a formalin-fixed paraffin-embedded (FFPE) human tissue sample and a formalin-fixed paraffin-embedded (FFPE) human tumor tissue sample. Exemplary PD-L1 expression immunohistochemistry tests include, without limitation, the PD-L1 IHC 22C3 PharmDx (FDA approved, Daco), Ventana PD-L1 SP263 assay, and the tests described in PCT/EP2017/073712.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, and rabbit) and most preferably a human. "Treatment", as used in a clinical setting, is intended for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of tumor, remission of a disease (e.g., cancer), decreasing symptoms resulting from a disease (e.g., cancer), increasing the quality of life of those suffering from a disease (e.g., cancer), decreasing the dose of other medications required to treat a disease (e.g., cancer), delaying the progression of a disease (e.g., cancer), curing a disease (e.g., cancer), and/or prolong survival of patients having a disease (e.g., cancer).

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen binding fragments thereof (such as Fab, Fab', F(ab')2, Fv), single chain (scFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., PD-L1). Antigen binding functions of an antibody can be performed by fragments of an intact antibody. Examples of binding fragments encompassed within the term "antigen binding fragment" of an antibody include Fab; Fab'; F(ab')2; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "preferentially binds" or "specifically binds" (used interchangeably herein) to a target (e.g., PD-L1 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a PD-L1 epitope is an antibody that binds this epitope with greater affinity, avidity, more readily, and/or with greater duration than it binds to other PD-L1 epitopes or non-PD-L1 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

Avelumab entered phase 1 clinical trial in early 2013 and has since then advanced to phase 3 trials in several different tumor types such as MCC, NSCLC, RCC, gastric cancer, ovarian cancer and bladder cancer. The dosing regimen in these trials was 10 mg/kg Q2W. Provided herein are improved dosing regimens for avelumab which could achieve a better overall response rate than the current 10 mg/kg Q2W dosing regimen.

Table 1 below provides the sequences of the anti-PD-L1 antibody avelumab for use in the treatment method, medicaments and uses of the present invention. Avelumab is described in International Patent Publication No. WO2013/079174, the disclosure of which is hereby incorporated by references in its entirety.

TABLE 1

Anti-human-PD-L1 antibody Avelumab Sequences

| | |
|---|---|
| Heavy chain CDR1 (CDRH1) | SYIMM (SEQ ID NO: 1) |
| Heavy chain CDR2 (CDRH2) | SIYPSGGITFY (SEQ ID NO: 2) |
| Heavy chain CDR3 (CDRH3) | IKLGTVTTVDY (SEQ ID NO: 3) |
| Light chain CDR1 (CDRL1) | TGTSSDVGGYNYVS (SEQ ID NO: 4) |
| Light chain CDR2 (CDRL2) | DVSNRPS (SEQ ID NO: 5) |
| Light chain CDR3 (CDRL3) | SSYTSSSTRV (SEQ ID NO: 6) |
| Heavy chain variable region (VR) | EVQLLESGGGLVQPGGSLRLSCAASGFTFSSYIMMWV RQAPGKGLEVVVSSIYPSGGITFYADKGRFTISRDNS KNTLYLQMNSLRAEDTAVYYCARIKLGTVTTVDYWGQ GTLVTVSS (SEQ ID NO: 7) |
| Light chain VR | QSALTQPASVSGSPGQSITISCTGTSSDVGGYNYVSV VYQQHPGKAPKLMIYDVSNRPSGVSNRFSGSKSGNTA SLTISGLQAEDEADYYCSSYTSSSTRVFGTGTKVTVL (SEQ ID NO: 8) |
| Heavy chain | EVQLLESGGGLVQPGGSLRLSCAASGFTFSSYIMMWVR QAPGKGLEWVSSIYPSGGITFYADTVKGRFTISRDNSK NTLYLQMNSLRAEDTAVYYCARIKLGTVTTVDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV VDVSHEDPEVKFNWYVDGVEVHNAKTKPREEQYNSTYR VVSVLTVLHQDWLNGKEYKCKVSNKALPAPIEKTISKA KGQPREPQVYTLPPSRDELTKNQVSLTCLVKGFYPSDI AVEWESNGQPENNYKTTPPVLDSDGSFFLYSKLTVDKS RWQQGNVFSCSVMHEALHNHYTQKSLSLSPGK (SEQ ID NO: 9) |
| Light chain | QSALTQPASVSGSPGQSITISCTGTSSDVGGYNYVSWY QQHPGKAPKLMIYDVSNRPSGVSNRFSGSKSGNTASLT ISGLQAEDEADYYCSSYTSSSTRVFGTGTKVTVLGQPK ANPTVTLFPPSSEELQANKATLVCLISDFYPGAVTVAW KADGSPVKAGVETTKPSKQSNNKYAASSYLSLTPEQWK SHRSYSCQVTHEGSTVEKTVAPTECS (SEQ ID NO: 10) |

EXAMPLES

General methods for Examples 1-3: a population pharmacokinetic (PK) model was used to estimate individual exposure metrics using individual pharmacokinetic parameters for patients with MCC and NSCLC. The influence of exposure metrics ($C_{trough}$,) on response was explored via logistic regression and was applied to model the relationships between exposure and the overall response rate (ORR). In the figures for each example, the heavy dot on each vertical bar represents a summary statistic of the observed data, divided into quartiles. The X axis for each quartile represents the mean $C_{trough}$ of the patients in each of the quartiles and the Y axis represents the probability of response for the individual quartile and it is corresponding 95% confidence interval. The curved thin line represents the logistic regression model fit, about all the observed data along with the 95% prediction interval about the regression (shaded red area).

Example 1. $C_{trough}$ and ORR Correlation of 88 Patients in a Phase 3 MCC Trial 88 patients participated in a phase 3 MCC trial with the avelumab dosing of 10 mg/kg Q2W over one hour of IV infusion. Patients were divided into four quartiles based on the $C_{through}$ value of patients, with 22 patients in each quartile. The $C_{trough}$ value of each patient was calculated based on the existing model and the actual serum concentration of avelumab tested for each patient at various points during the trial. As shown in FIG. 1, the four quartiles of patients were represented by the four vertical bars in the figure. The $C_{trough}$ value of each quartile is represented by the mean $C_{trough}$ value of the quartile. The heavy dot on each vertical bar represents the probability of overall response rate for the group.

A positive correlation between $C_{trough}$ and ORR was observed (FIG. 1). Patients of the upper $4^{th}$ quartile have a probability of ORR of about 60% (FIG. 1). A mean $C_{trough}$ of around 44-50 ug/mL correlates to a probability of ORR of 50-60% (FIG. 1).

Figure 2:
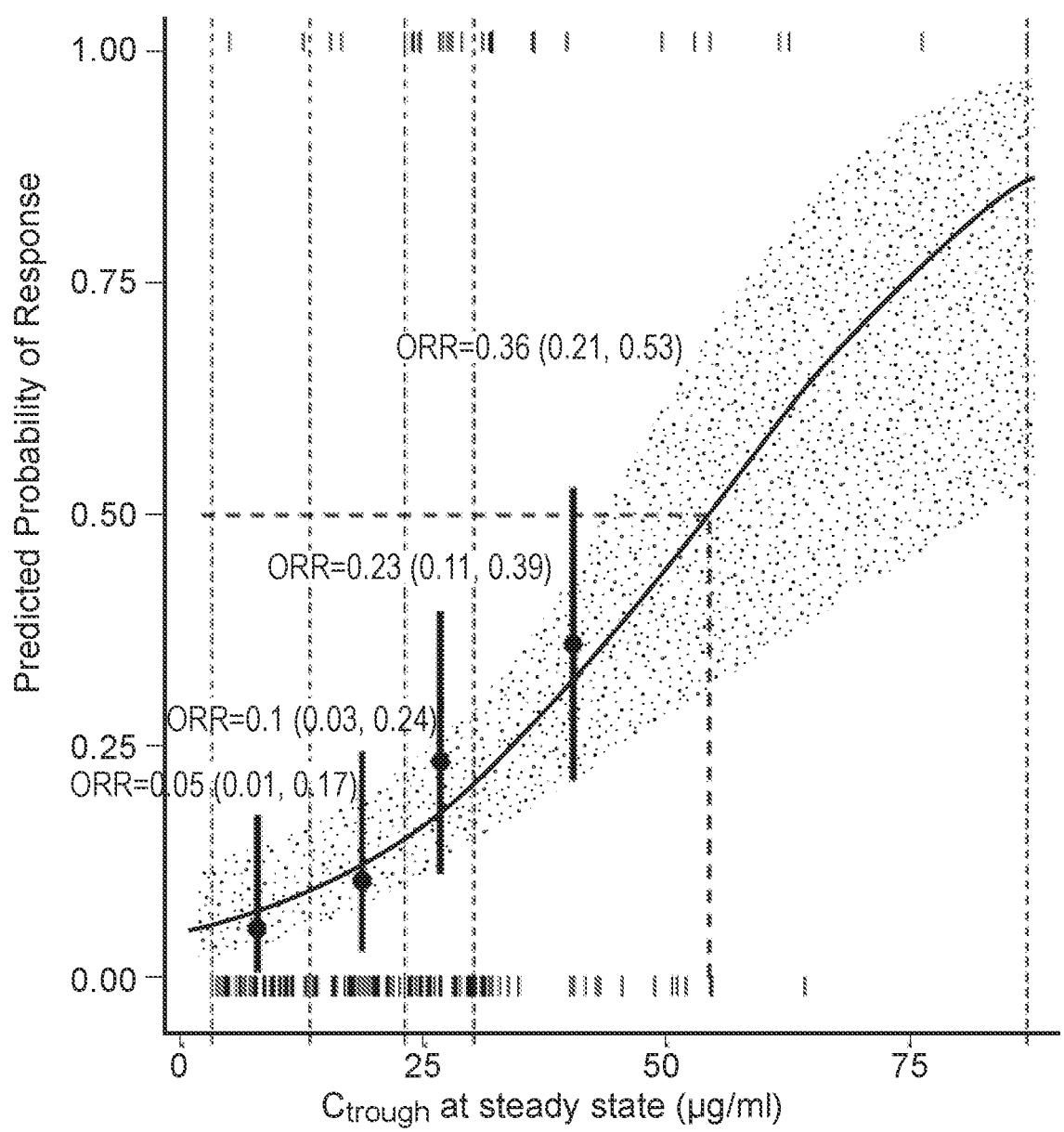

Example 2. $C_{trough}$ and ORR Correlation of 156 Patients in Phase 3 First Line NSCLC Trial 156 patients participated in a phase 3 first line NSCLC trial with the avelumab dosing of 10 mg/kg Q2W over one hour of IV infusion. Patients were divided into four quartiles based on the $C_{through}$ value of patients, with 39 patients in each quartile. The $C_{trough}$ number of each patient was calculated based on the existing model and the actual serum concentration of avelumab tested for each patient at various points during the trial. As shown in FIG. 2, the four quartiles of patients were represented by the four vertical bars in the figure. The $C_{trough}$ value of each quartile is represented by the mean $C_{trough}$ value of the quartile. The heavy dot on each vertical bar represents the probability of overall response rate for the group.

A positive correlation between $C_{trough}$ and ORR was observed (FIG. 2). Patients of the upper $4^{th}$ quartile have a probability of ORR of about 35% (FIG. 2). A mean $C_{trough}$ of around 44-54 ug/mL correlates to a probability of ORR of 35-50% (FIG. 2).

Figure 3:
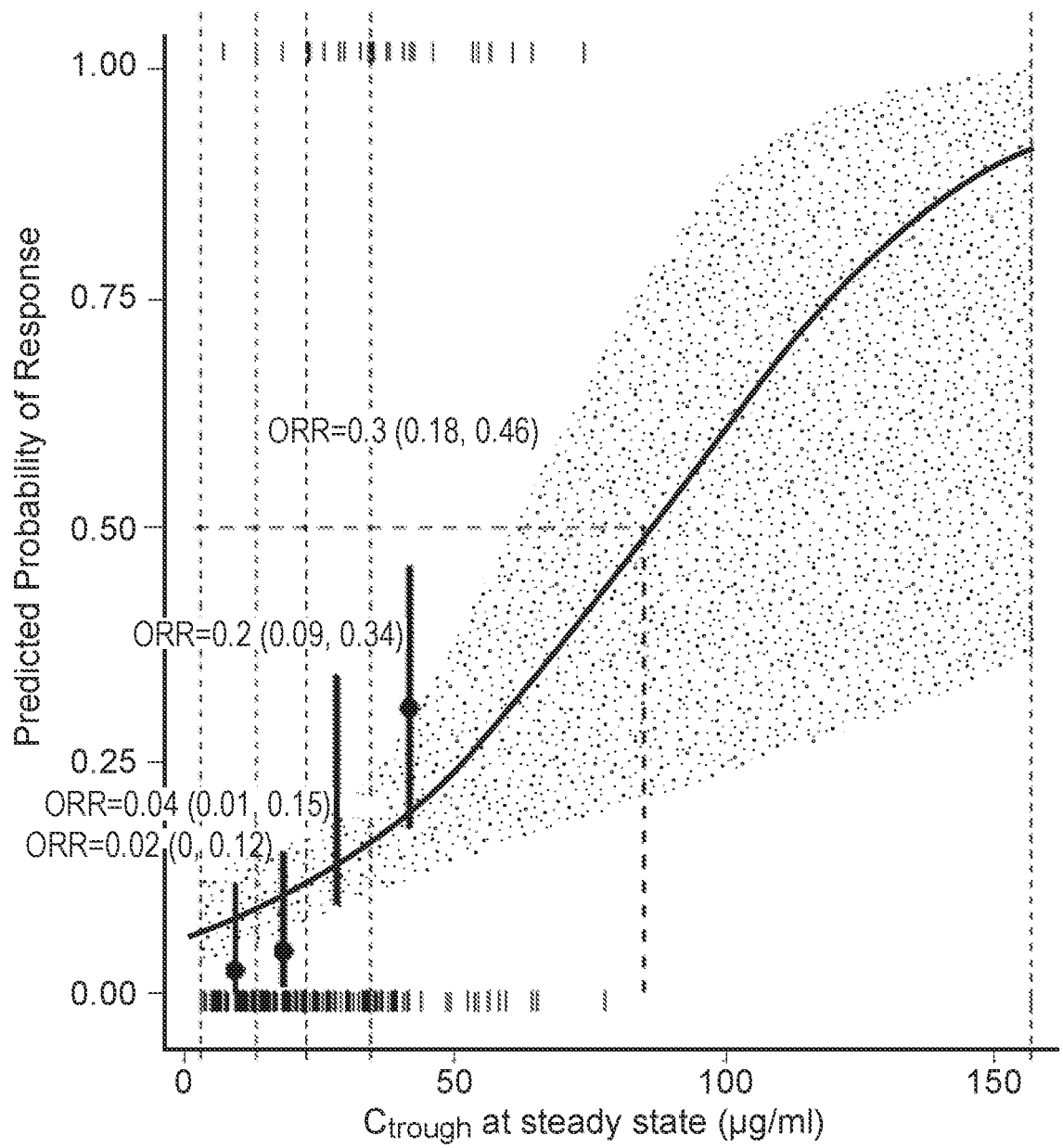

Example 3. $C_{trough}$ and ORR Correlation of 184 Patients in Phase 1b Second Line NSCLC Trial 184 patients participated in a phase 1b second line NSCLC trial with the avelumab dosing of 10 mg/kg Q2W over one hour of IV infusion. Patients were divided into four quartiles based on the $C_{through}$ value of patients, with 46 patients in each quartile. The $C_{trough}$ number of each patient was calculated based on the existing model and the actual serum concentration of avelumab tested for each patient at various points during the trial. As shown in FIG. 3, the four quartiles of patients were represented by the four vertical bars in the figure. The $C_{trough}$ value of each quartile is represented by the mean $C_{trough}$ value of the quartile. The heavy dot on each vertical bar represents the probability of overall response rate for the group.

A positive correlation between $C_{trough}$ and ORR was observed. Patients of the upper $4^{th}$ quartile have a probability of ORR of about 31% (FIG. 3). A mean $C_{trough}$ around 60-85 ug/mL correlates to a probability of ORR of 35-50% (FIG. 3).

Tumor proportion score (TPS) of PD-L1 expression was tested of the tumor tissues collected during the clinical trial. TPS of PD-L1 expression was analyzed together with $C_{through}$ and response rate. Surprising ORRs were observed among the subset of patients with both high exposure any increased PD-L1 expression in the tumor cells. Among the 184 patients, 142 patients evaluated for $C_{trough}$ exposure, and 71 patients were in the upper half (top two quartiles). For patients in the upper half (top two quartiles) of the $C_{trough}$ exposure, TPS PD-L1 expression cutoff values of ≥1%, ≥5%, ≥50%, and ≥80% yielded ORRs of 25.4%, 25.6%, 33.3%, and 42.9%, respectively (Table 2).

TABLE 2

Avelumab response in 2L NSCLC patients with high exposure and high TPS of PD-L1

| PD-L1 TPS | Patient number | ORR |
|---|---|---|
| Non selected | 184 | 14.1% |
| 1% and above | 59 | 25.4% |
| 5% and above | 39 | 25.6% |
| 50% and above | 21 | 33.3% |
| 80% and above | 14 | 42.9% |

A consistent positive correlation between mean $C_{trough}$ and the probability of ORR was observed (Examples 1-3). Taking into consideration of the best probability of the ORR in each Example, which occurs generally in the $4^{th}$ quartile (Examples 1-3), the correlation of the $C_{trough}$ and ORR is expected to continue within reasonable range above the $4^{th}$ quartile. These data indicate that a mean $C_{trough}$ of 44-85 ug/mL correlates with a probability of ORR of 50% in various tumor types.

Example 4. Simulation of $C_{trough}$ of Various Avelumab Dosing Regimens

Table 3 provides a number of dosing regimens for avelumab. The population PK model generated for avelumab based on previous work, was used to simulate the $C_{trough}$ of selected dosing regimens, in MCC, SCCLC and in solid tumor types.

TABLE 3

Avelumab dosing regimens

| Proposed dosing regimen | Notes |
|---|---|
| 5-10 mg/kg Q1W | Dosing range |
| 10 mg/kg Q1W | Preferred specific dose |
| 5 mg/kg Q1W | additional Preferred specific dose within the range |
| 8 mg/kg Q1W | |
| 11-20 mg/kg Q2W | Dosing range |
| 11 mg Q2W | Preferred specific dose |
| 20 mg/kg Q2W | Preferred specific dose |
| 13, 15, 17 mg/kg Q2W | Additional preferred specific dose |
| 15-30 mg/kg Q3W | Range |
| 20 mg/kg Q3W | Preferred specific doses |
| 15, 20, 25, 30 mg/kg Q3W | Additional Preferred specific dose within the range |
| 5-20 mg/kg Q1W for n weeks followed by 10 mg/kg Q2W | Dosing range n is 6 or 12 |
| 10 mg/kg Q1W for 12 weeks followed by 10 mg/kg Q2W | Preferred specific dose |

TABLE 3-continued

Avelumab dosing regimens

| Proposed dosing regimen | Notes |
|---|---|
| 5, 15, 20 mg/kg Q1W for 6 or 12 weeks followed by 10 mg/kg Q2W | Additional Preferred specific dose within the range |
| 500-800 mg Q1W | Correspond to 5-10 mg/kg Q1W |
| 900-1600 mg Q2W | Correspond to 11-20 mg/kg Q2W |
| 1250-2400 mg Q3W | Correspond to 15-30 mg/kg Q2W |
| 500-1600 mg Q1W for n weeks followed by 800 mg Q2W | Correspond to 5-20 mg/kg Q1W for n weeks followed by 10 mg/kg Q2W |

General methods: Pharmacokinetic simulations of the avelumab dosing regimens were performed using the NON-MEM version 7.3 software (ICON Development Solutions, Hanover, Md.). Two compartment IV model with linear elimination was used as the population PK model. This model is based on over three thousand PK observations from over seven hundred patients who participated in the avelumab clinical trials thus far. To conduct the simulations of the dosing regimen described in above Table 3, a dataset was created with dosing events, dosing amounts, a 1 hour rate of infusion, and covariates included in the population PK model. The steady-state $C_{trough}$ concentrations were calculated by removing the first 3 doses and then computing the average $C_{trough}$ from the remaining dosing event for the given dose amount. For loading dose schedules, the $C_{trough}$ was calculated for the loading portion of the regimen as well as for the continued dosing after the loading period.

Results of the above simulation are shown in the below Tables 4-6.

TABLE 4

Summary of median $C_{trough}$ for MCC under various dosing regimen

| No. | Dosing regimen | Median $C_{trough}$ (ug/mL) | 95% $C_{trough}$ prediction interval (ug/mL) |
|---|---|---|---|
| 1 | 5 mg/kg Q1W | 59 | 29.0-109.8 |
| 2 | 10 mg/kg Q1W | 116.5 | 56.3-208.5 |
| 3 | 10 mg/kg/Q2W | 38.9 | 14.7-83.0 |
| 4 | 11 mg/kg Q2W | 43.4 | 17.6-91.5 |
| 5 | 20 mg/kg Q2W | 77.1 | 31.1-160.3 |
| 6 | 10 mg/kg Q3W | 18.1 | 4.5-45.5 |
| 7 | 15 mg/kg Q3W | 27.3 | 9.5-67.4 |
| 8 | 20 mg/kg Q3W | 36.6 | 12.3-86.7 |
| 9 | 25 mg/kg Q3W | | |
| 10 | 30 mg/kg Q3W | 53.7 | 18.4-127.2 |
| 11 | 5 mg/kg Q1W for 12 weeks followed by 10 mg/kg Q2W | During Loading: 59.0 After loading: 40.6 | During loading: 29.0-109.8 After loading: 15.7-90.2 |
| 12 | 10 mg/kg Q1W for 12 weeks followed by 10 mg/kg Q2W | During Loading: 116.5 After loading: 45.3 | During loading: 56.3-208.5 After loading: 17.4-100.4 |
| 13 | 20 mg/kg Q1W for 12 weeks followed by 10 mg/kg Q2W | During loading 225.8 After loading: 55.3 | During loading: 115.4-430.3 After loading: 17.4-100.4 |
| 14 | 5 mg/kg Q1W for 6 weeks followed by 10 mg/kg Q2W | During loading: 55.0 After loading: 39.4 | During loading: 27.6-105.4 After loading: 16.2-88.3 |
| 15 | 10 mg Q1W for 6 weeks followed by 10 mg/kg Q2W | During loading: 110.1 After loading: 41.9 | During loading: 53.6-206.0 After loading: 17.1-88.3 |

TABLE 4-continued

Summary of median $C_{trough}$ for MCC under various dosing regimen

| No. | Dosing regimen | Median $C_{trough}$ (ug/mL) | 95% $C_{trough}$ prediction interval (ug/mL) |
|---|---|---|---|
| 16 | 20 mg Q1W for 6 weeks followed by 10 mg/kg Q2W | During loading: 215.7 After loading: 46.2 | During loading: 107.7-382.6 After loading: 17.9-105.2 |

The dosing regimens Nos. 1-2, 4-5, 8-16 of Table 4, and ranges within these regimens such as 5-10 mg/kg Q1W, 11-20 mg/kg Q2W, 20-30 mg/kg Q3W, 5-20 mg/kg Q1W for 6-12 weeks followed by 10 mg/kg Q2W, provide an expected median $C_{trough}$ higher than the current 10 mg/kg Q2W dosing regimen (Table 4). From Example 1, a dosing regimen that provides a mean $C_{trough}$ of over 50 ug/mL correlates with a higher probability of ORR in MCC. The data shown in Table 4 for the avelumab dosing regimens 1-2, 10 and 11-16 indicate that these regimens could advantageously provide a higher expected probability of ORR for MCC.

TABLE 5

Summary of Median $C_{trough}$ under various dosing regimen for NSCLC.

| No. | Dosing regimen | Median Ctrough (ug/mL) | 95% $C_{trough}$ prediction interval (ug/mL) |
|---|---|---|---|
| 1 | 5 mg/kg Q1W | 42.8 | 19.4-79.6 |
| 2 | 10 mg/kg Q1W | 83.9 | 39.9-160.2 |
| 3 | 10 mg/kg/Q2W | 20.6 | 4.8-51.2 |
| 4 | 11 mg/kg Q2W | 22.2 | 5.8-56.6 |
| 5 | 20 mg/kg Q2W | 39.9 | 11.5-96.3 |
| 6 | 10 mg/kg Q3W | 6.3 | 0.0-20.1 |
| 7 | 15 mg/kg Q3W | 9.1 | 0.2-34.1 |
| 8 | 20 mg/kg Q3W | 12.8 | 0.5-46.7 |
| 9 | 25 mg/kg Q3W | 14.2 | 0.9-54.6 |
| 10 | 30 mg/kg Q3W | 17.6 | 1.8-66.7 |
| 11 | 5 mg/kg Q1W for 12 weeks followed by 10 mg/kg Q2W | During Loading: 42.8 After loading: 20.2 | During loading: 19.4-79.6 After loading: 5.2-47.5 |
| 12 | 10 mg/kg Q1W for 12 weeks followed by 10 mg/kg Q2W | During loading: 83.9 After loading: 20.2 | During loading: 39.9-160 After loading: 4.8-51.5 |
| 13 | 20 mg/kg Q1W for 12 weeks followed by 10 mg/kg Q2W | During loading 172.9 After loading: 20.5 | During loading: 74.6-342.6 After loading: 4.6-63.9 |
| 14 | 5 mg/kg Q1W for 6 weeks followed by 10 mg/kg Q2W | During loading: 42.9 After loading: 20.9 | During loading: 19.5-82.1 After loading: 5.2-51.7 |
| 15 | 10 mg Q1W for 6 weeks followed by 10 mg/kg Q2W | During loading: 86.7 After loading: 20.5 | During loading: 39.0-163 After loading: 5.0-52.6 |
| 16 | 20 mg Q1W for 6 weeks followed by 10 mg/kg Q2W | During loading: 163.4 After loading: 19.6 | During loading: 79.3-332.5 After loading: 4.9-56.4 |

The dosing regimens Nos. 1-2, 4-5, 10, 11-16 of Table 5, and ranges within these regimens, such as 5-10 mg/kg Q1W, 11-20 mg/kg Q2W, 5-20 mg/kg Q1W for 6-12 weeks followed by 10 mg/kg Q2W, provide an expected median $C_{trough}$ above the current 10 mg/kg Q2W dosing regimen (Table 5). Examples 1-3 above demonstrate that the mean $C_{trough}$ has a positive correlation with the probability of ORR. In Examples 2 and 3, a mean $C_{trough}$ of 44 ug/mL to 85 ug/mL corresponds to about 35% to about 50% probability of ORR, wherein the $4^{th}$ quartile probability of ORR in Examples 2 and 3 was 35% and 31% respectively. The data from Table 5 demonstrate that regimens Nos. 1-2, 5 and 11-16 provide an expected mean $C_{trough}$ of about or over 44 ug/mL and thus could advantageously provide better probability of ORR in NSCLC patients. Other advantageous dosing regimens include, for example, regimens Nos. 2, 12-13 and 15-16, and the ranges within these regimens such as 10 mg-20 mg/kg Q1W for 6 or 12 weeks followed by 10 mg/kg Q2W, all of which correspond to a median $C_{trough}$ of about or more than 85 ug/mL. Other advantageous regimens for NSCLC are those providing a mean $C_{trough}$ between 44 ug/mL and 85 ug/ml, i.e. dosing regimen Nos. 1, 2, 5, 11, 12, 14, 15 of Table 5, and ranges within these regimens such as 5-10 mg/kg Q1W, 5-10 mg/kg Q1W for 6-12 weeks followed by 10 mg/kg Q2W.

TABLE 6

Summary of Median $C_{trough}$ under various avelumab dosing regimen for all solid tumor types.

| No. | Dosing regimen | Median $C_{trough}$ (ug/mL) | 95% $C_{trough}$ prediction interval (ug/mL) |
|---|---|---|---|
| 1 | 5 mg/kg Q1W | 43 | 19.5-84 |
| 2 | 10 mg/kg Q1W | 83.6 | 36.6-160 |
| 3 | 10 mg/kg/Q2W | 19.9 | 4.7-53.3 |
| 4 | 11 mg/kg Q2W | 22.9 | 6.4-57.9 |
| 5 | 20 mg/kg Q2W | 40.2 | 11.1-100.5 |
| 6 | 10 mg/kg Q3W | 6.3 | 0.0-33.5 |
| 7 | 15 mg/kg Q3W | 9.2 | 0.0-33.5 |
| 8 | 20 mg/kg Q3W | 11.6 | 0.4-41.9 |
| 9 | 25 mg/kg Q3W | | |
| 10 | 30 mg/kg Q3W | 16.7 | 1.7-58.2 |
| 11 | 5 mg/kg Q1W for 12 weeks followed by 10 mg/kg Q2W | During Loading: 43.0 After loading: 20.2 | During loading: 19.5-84.5 After loading: 4.7-53.2 |
| 12 | 10 mg/kg Q1W for 12 weeks followed by 10 mg/kg Q2W | During loading: 83.6 After loading: 19.7 | During loading: 36.6-160 After loading: 4.3-51.6 |
| 13 | 20 mg/kg Q1W for 12 weeks followed by 10 mg/kg Q2W | During loading 160.7 After loading: 19.3 | During loading: 73.8-319 After loading: 4.2-54.9 |
| 14 | 5 mg/kg Q1W for 6 weeks followed by 10 mg/kg Q2W | During loading: 42.2 After loading: 20.9 | During loading: 19.6-83.7 After loading: 5.1-51.1 |
| 15 | 10 mg Q1W for 6 weeks followed by 10 mg/kg Q2W | During loading: 83.9 After loading: 19.9 | During loading: 39.6-158 After loading: 5.5-48.6 |
| 16 | 20 mg Q1W for 6 weeks followed by 10 mg/kg Q2W | During loading: 163.8 After loading: 19.9 | During loading: 78.0-31 After loading: 5.3-52.0 |

Avelumab dosing regimen Nos. 1-2, 4-5, 11-16 in Table 6, and ranges within these regimens such as 5-10 mg/kg Q1W, 11-20 mg/kg Q2W, 5-20 mg/kg Q1W for 6-12 weeks followed by 10 mg/kg Q2W, provide an expected median $C_{trough}$ above the current 10 mg/kg Q2W dosing regimen, and could advantageously provide a better probability of ORR (see, Examples 1-3). From Examples 1-3, a mean $C_{trough}$ of 44-85 ug/mL corresponds to about 50% of ORR respectively. Thus, dosing regimens that provide a mean $C_{trough}$ of over 44 ug/mL could advantageously provide a higher probability of ORR in patients with solid tumors. As such, dosing regimen 1-2, 5 and 11-16 shown in Table 6, or ranges therein, such as 5-10 mg/kg Q1W, 5-20 mg/kg Q1W for 6 or 12 weeks followed by 10 mg/kg Q2W, are advantageous for treatment of solid tumor types. Other advantageous dosing regimens to treat solid tumor include avelumab dosing regimen Nos. 2, 12-13 and 15-16 and the ranges within these regimens such as 10 mg-20 mg/kg Q1W for 6 or 12 weeks followed by 10 mg/kg Q2W, all of which corresponding to a median $C_{trough}$ of about or more than 85 ug/mL. Other advantageous avelumab dosing regimens include dosing regimen Nos. 1-2, 5, 11-12 and 14-15 shown in Table 6, and ranges within these regimens such as, for example, 5-10 mg/kg Q1W, 5-10 mg/kg Q1W for 6 or 12 weeks followed by 10 mg/kg Q2W, all of which correspond to a median $C_{trough}$ between about 44 ug/mL and about 85 ug/mL in solid tumors. Exemplary solid tumor types suitable for treatment with the avelumab dosing regimens provided herein include, without limitation, MCC, NSCLC, RCC, bladder cancer, ovarian cancer, head and neck cancer, gastric cancer, mesothelioma, urothelial carcinoma, breast cancer, adenocarcinoma of the stomach and thymoma.

Example 5. Modeling of Safety and Efficacy for the 800 mg Q2W Dosing in Comparison with the 10 mg/kg Q2W Dosing The clinical profile of avelumab has been evaluated from data in more than 1800 subjects in ongoing Phase I, II, and III trials in adult subjects with various solid tumors. The clinical pharmacology results are obtained from 1827 subjects from three studies with PK information available as of Jun. 9, 2016 (studies EMR100070-001 and EMR100070-003) and Nov. 20, 2015 (study EMR100070-002).

Exposure Metrics.

Figure 4A:
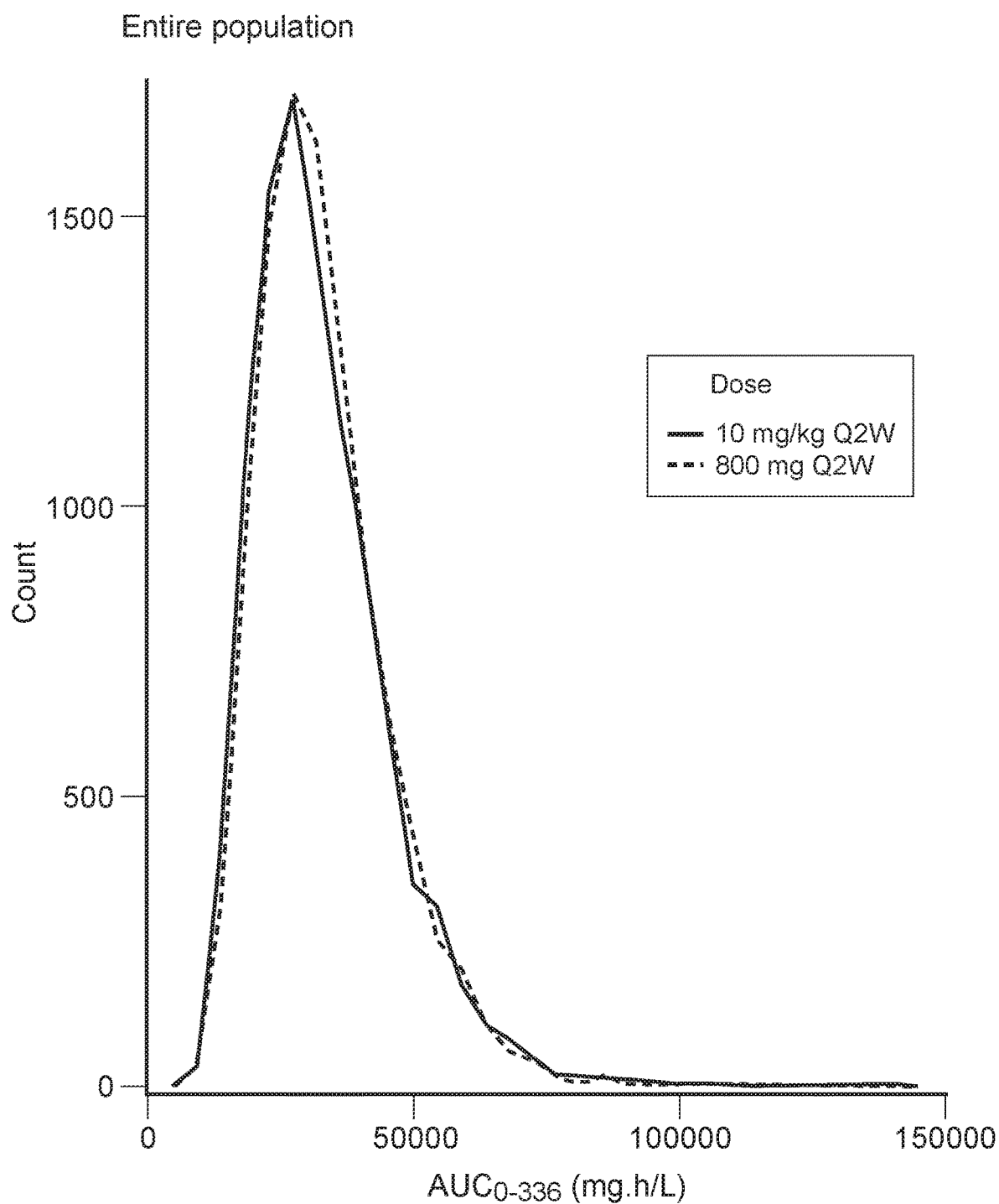

Based on the clinical pharmacology results of these more than 1800 subjects mentioned above, 10000 and 4000 simulated subjects were generated using the PK CYCLE model and PK SS model respectively to project the avelumab exposure metrics of AUC, $C_{though}$ and $C_{max}$ for both the 10 mg/kg Q2W dosing and the 800 mg Q2W dosing. Where PK CYCLE model represents the PK model generated using PK data from the first dose of avelumab and PK SS model represents the PK model generated using PK data after repeated dosing of avelumab. Such projected exposure metrics were then used in the below Exposure-efficacy correlation and Exposure-safety correlation simulation. The distribution plot of such projected avelumab $AUC_{0-336}$ are shown in FIG. 4A, FIG. 4B, FIG. 5A and FIG. 5B. The plots depicted in FIG. 4A and FIG. 4B show that the simulated values of $AUC_{0-336}$ have a close correspondence between the two dosing regimens. The graphs in FIG. 5A and FIG. 5B show that the total variability of avelumab $AUC_{0-336}$ is lower in the 800 mg Q2W regimen than the 10 mg/kg Q2W regimen.

Exposure—Efficacy Correlation and Exposure—Safety Correlation.

A univariate logistic regression model has been developed to describe the exposure—best overall response (BOR) relationship for the n=88 observed subjects with mMCC. The exposure values that were used for developing the logistic regression model were simulated from the PK CYCLE and PK SS models. Four hundred sets of parameter estimates were sampled from the uncertainty distribution of the exposure-BOR logistic regression model. For each of these 400 parameter sets, 2500 subjects were sampled from the mMCC population of the n=10000 subjects simulated based on the PK CYCLE and PK SS models. The mean predicted probability of response (across the n=2500 simulated subjects) was then obtained for each of the 400 sets of logistic model parameter estimates.

The same procedure was followed for the UC indication, with n=153 observed subjects with UC.

Figure 6:
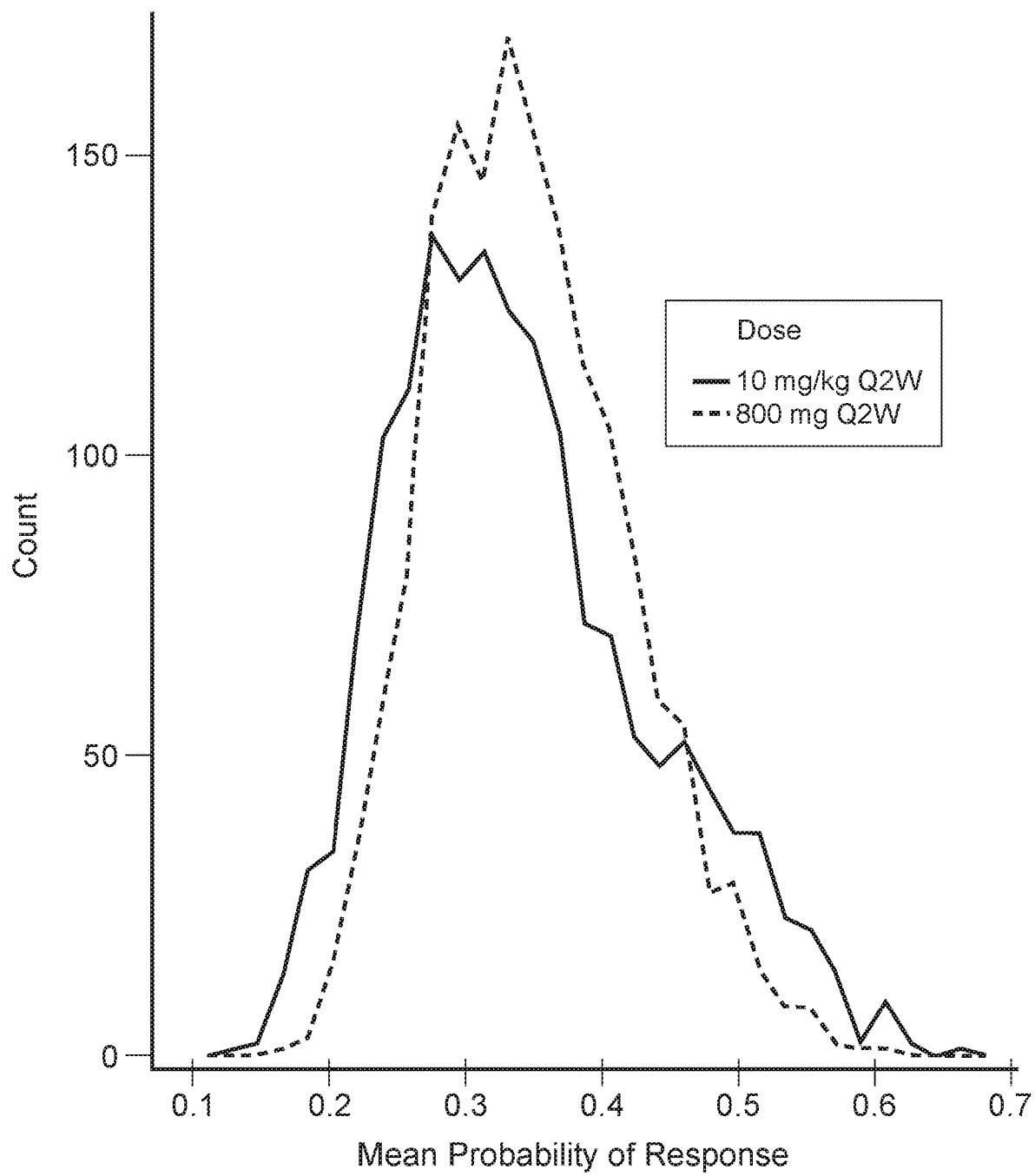
FIG. 6 depicts the density plot of mean probability of best overall response (BOR) in simulated studies with metastatic MCC (mMCC) based on the PK CYCLE model, for the 10 mg/kg Q2W and the 800 mg Q2W dose.
Figure 7:
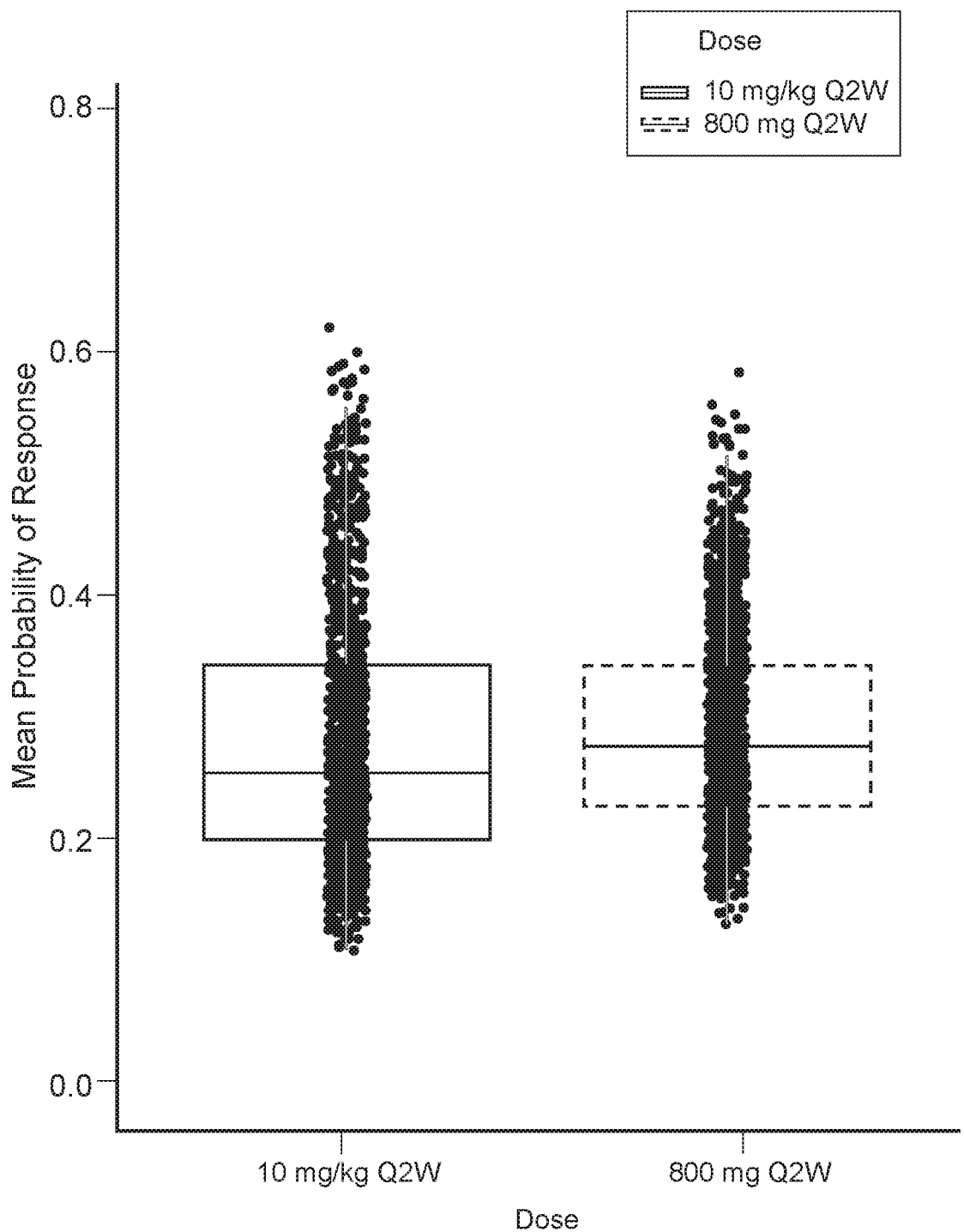
FIG. 7 depicts the box and whisker plot of mean probability of BOR in simulated studies with UC for the 10 mg/kg Q2W and 800 mg Q2W.

The results are summarized in the graphs shown in FIG. 6 and FIG. 7. The graph in FIG. 6 shows the probability of BOR in individual simulated patients with mMCC have large overlap between, and are similar for the 10 mg/kg Q2W and the 800 mg Q2W dosing regimens. The graph in FIG. 7 shows that the mean probability of BOR is very similar between the 10 mg/kg Q2W and 800 mg Q2W dosing regimens for the UC with a lower variability for the 800 mg Q2W dosing.

Figure 8A:
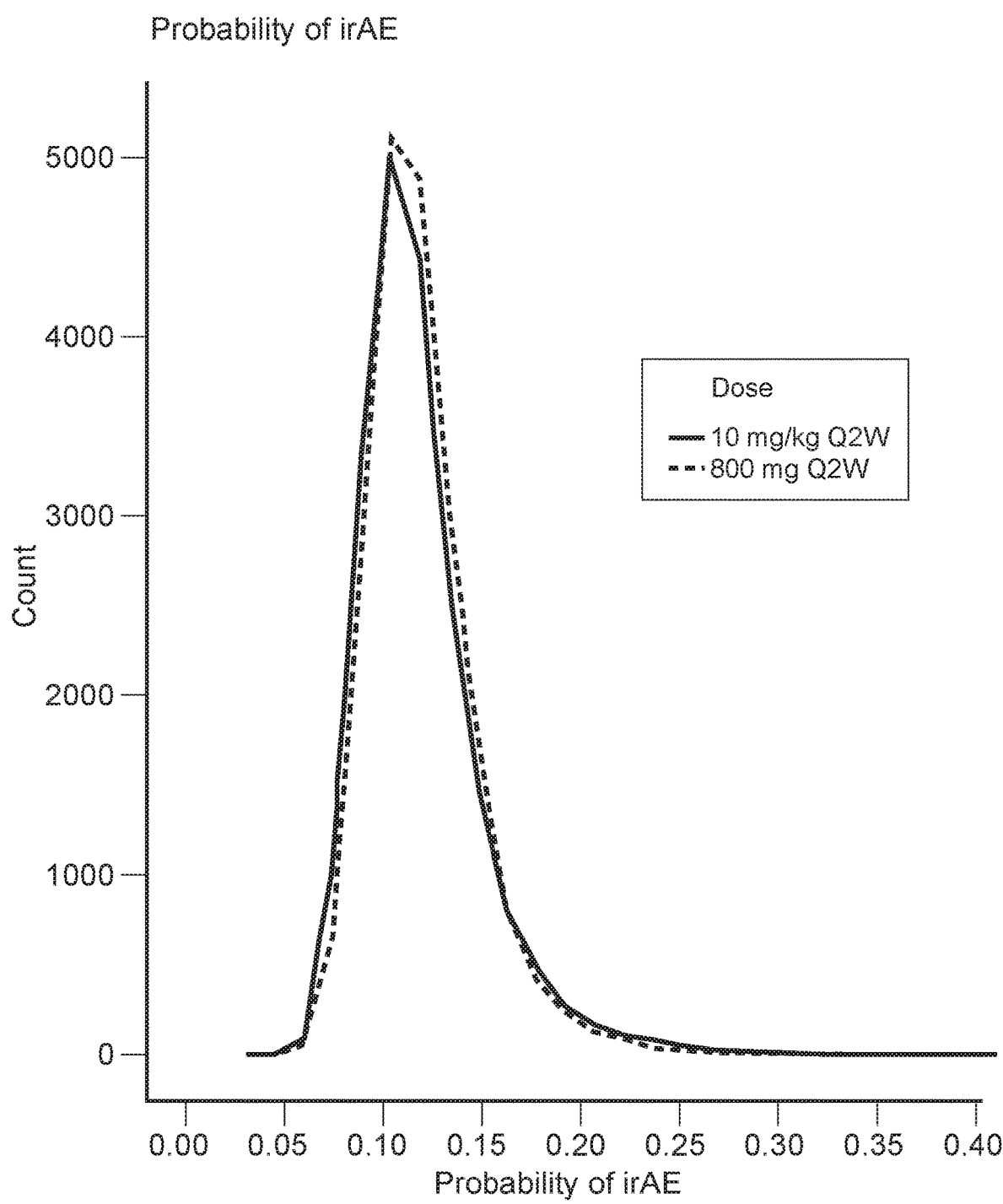
FIG. 8A and FIG. 8B depict the density plot (FIG. 8A) and box and whisker plot (FIG. 8B), using the PK CYCLE model, showing the probably of experiencing an immune-related adverse event (irAE) after 10 mg/kg Q2W and 800 mg Q2W dose.
Figure 8B:
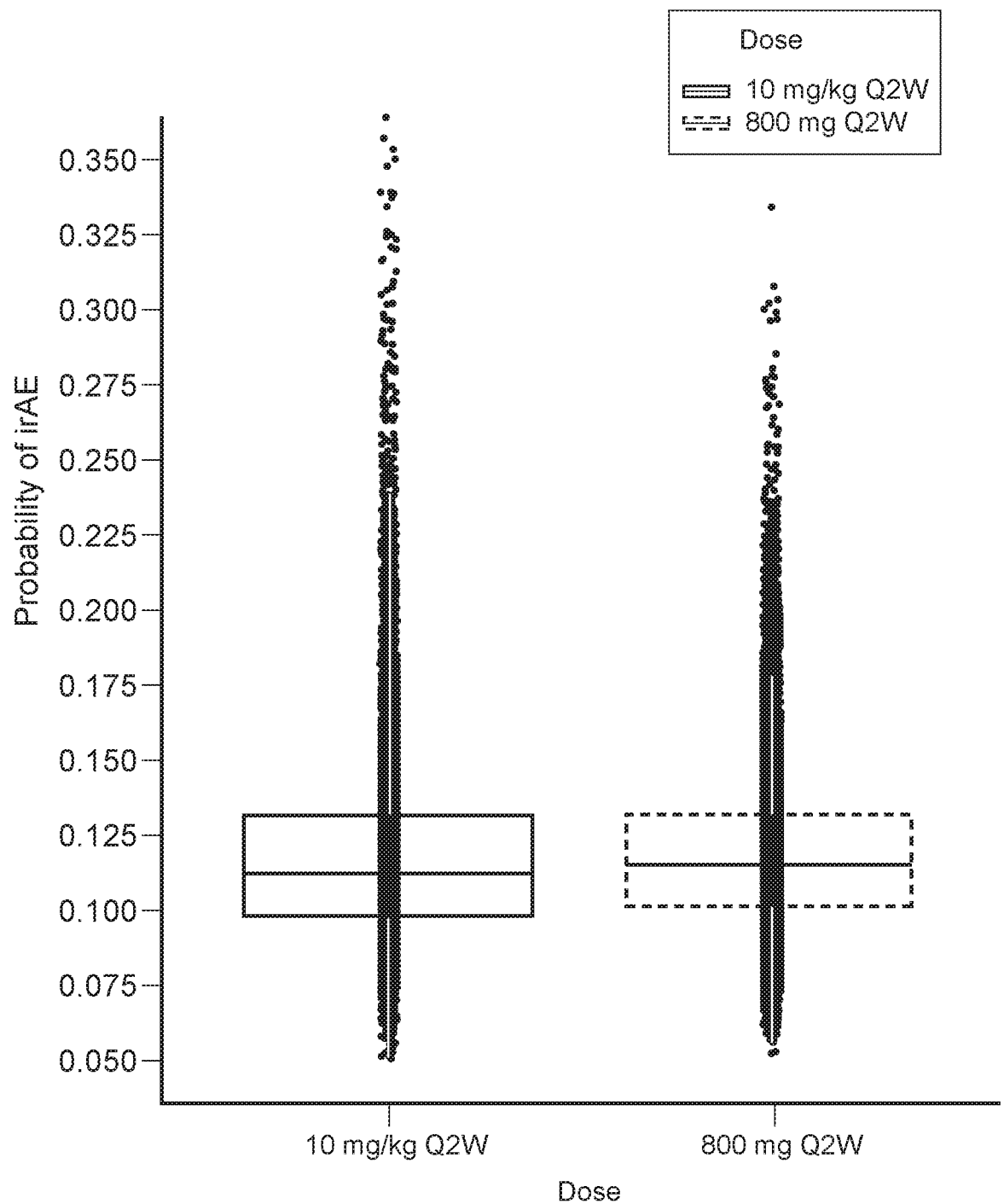
Figure 9B:
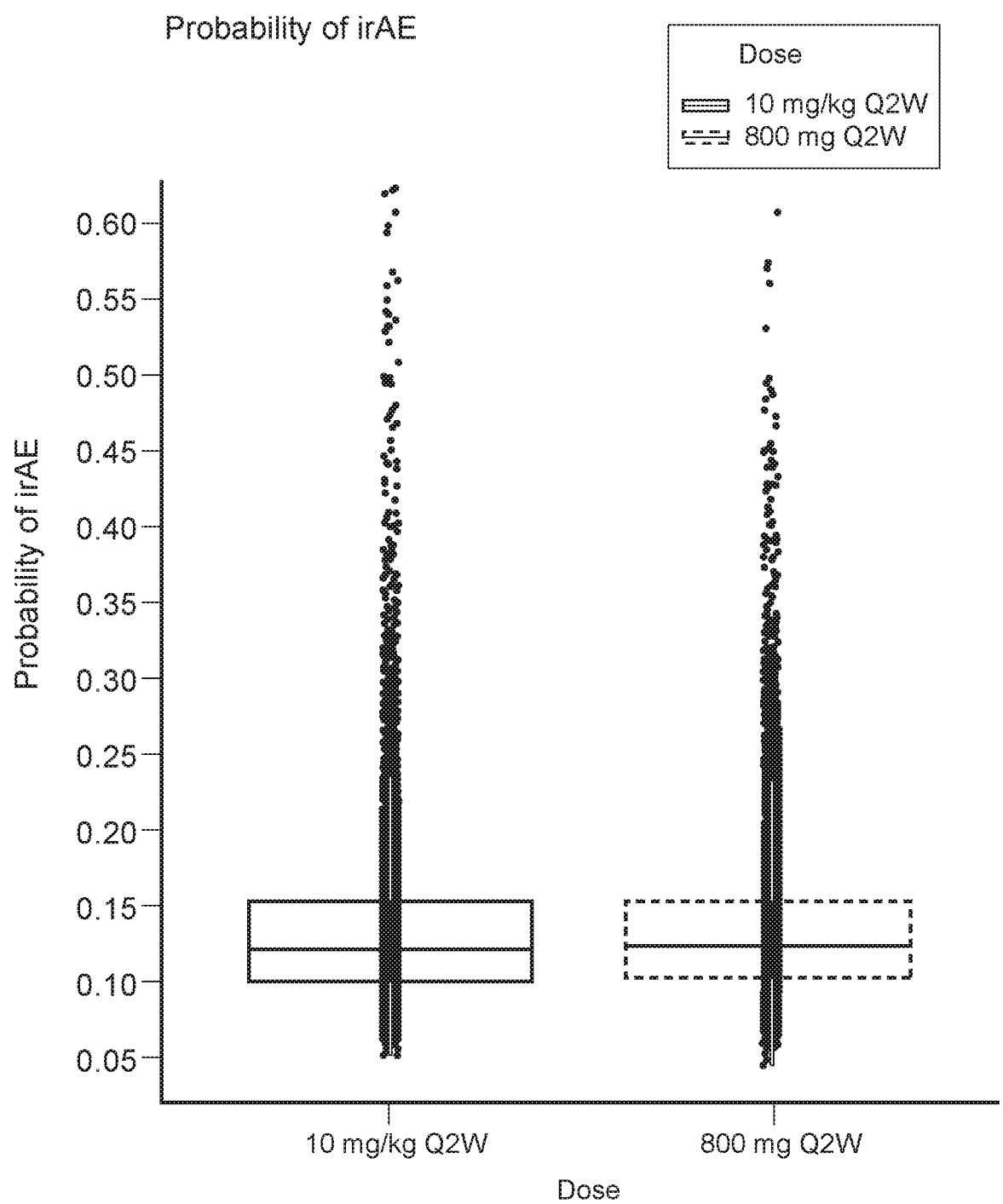

Exposure—safety correlation was modelled similarly using the safety variables immune related AE of any grade (irAE) and infusion related reactions (IRR). The results are shown in FIG. 8A, FIG. 8B, FIG. 9A and FIG. 9B. The graphs depicted in FIG. 8A and FIG. 8B show very similar probability of experiencing an irAE between the two dosing regimens. The graphs depicted in FIG. 9A and FIG. 9B show that the 800 mg Q2W dosing regimen tends to have a lower variability comparing to the 10 mg/kg Q2W dosing.

The invention claimed is:

1. A method of treating a cancer in a patient, comprising administering avelumab to the patient according to a dosing regimen of X mg/kg Q1W for n weeks followed by Y mg/kg Q2W, wherein X is 5-20, Y is 10-20, n is 6, 12 or 18.

2. The method of claim 1, wherein X is 10, Y is 10, n is 12.

3. The method of claim 1, wherein X is 10, Y is 10, n is 6.

4. The method of claim 1, wherein the cancer is selected from the group consisting of MCC, NSCLC, RCC, bladder cancer, ovarian cancer, head and neck cancer and gastric cancer.

5. The method of claim 4, wherein the cancer is NSCLC.

6. A method of treating a cancer in a patient, comprising administering avelumab to the patient according to a dosing regimen of 400-1600 mg Q1W for n weeks followed by 800-1600 mg Q2W, wherein n is 6, 12 or 18.

7. The method of claim 6, wherein the dosing regimen is 800 mg Q1W for n weeks, followed by 800 mg Q2W, n is 6 or 12.

8. The method of claim 7, wherein n is 12.

9. The method of claim 7, n is 6.

10. The method of claim 6, wherein the dosing regimen is 1200 mg Q1W for n weeks followed by 800 mg Q2W, wherein n is 12.

11. The method of claim 6, wherein the cancer is selected from the group consisting of MCC, NSCLC, RCC, bladder cancer, ovarian cancer, head and neck cancer and gastric cancer.

12. The method of claim 11, wherein the cancer is NSCLC.

13. A method of treating a cancer in a patient, comprising administering avelumab to the patient according to a dosing regimen of 400-800 mg flat dose Q2W.

14. The method of claim 13, wherein the dosing regimen is 800 mg flat dose Q2W.

15. The method of claim 13, wherein the cancer is selected from the group consisting of MCC, NSCLC, RCC, bladder cancer, ovarian cancer, head and neck cancer and gastric cancer.

16. The method of claim 13, wherein the cancer is NSCLC.

17. The method of claim 6, wherein the dosage regimen results in cancer has a tumor proportion score of PD-L1 expression of 1% or above, 5% or above, 10% or above, 20% or above, 30% or above, 40% or above, 50% or above, 60% or above, 70% or above, 80% or above, or 95% or above.

18. The method of claim 17, wherein the tumor proportion score of PD-L1 expression is 50% or above.

19. A method of treating a cancer in a patient, comprising administering avelumab to the patient according to a dosing regimen selected from the group consisting of 800 mg Q1W for 12 weeks followed by 800 mg Q2W and 10 mg/kg Q1W for 12 weeks followed by 10 mg/kg Q2W, and wherein the cancer has a tumor proportion score of PD-L1 expression of 5% or above, 20% or above, 50% or above or 80% or above.

20. The method of claim 19, wherein the tumor proportion score of PD-L1 expression is 50% or above and cancer is non-small cell lung cancer.

* * * * *

UNITED STATES PATENT AND TRADEMARK OFFICE
CERTIFICATE OF CORRECTION

PATENT NO. : 11,274,154 B2
APPLICATION NO. : 16/339779
DATED : March 15, 2022
INVENTOR(S) : Glen Ian Andrews et al.

Page 1 of 1

It is certified that error appears in the above-identified patent and that said Letters Patent is hereby corrected as shown below:

In the Claims

Claim 17, Column 24, Lines 45-46, delete "dosage regimen results in"

Signed and Sealed this
Tenth Day of May, 2022

Katherine Kelly Vidal
*Director of the United States Patent and Trademark Office*

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthetic Consruct

<400> SEQUENCE: 1

Ser Tyr Ile Met Met
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct
```

-continued

<400> SEQUENCE: 2

Ser Ile Tyr Pro Ser Gly Gly Ile Thr Phe Tyr
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Ile Lys Leu Gly Thr Val Thr Thr Val Asp Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Construct

<400> SEQUENCE: 4

Thr Gly Thr Ser Ser Asp Val Gly Gly Tyr Asn Tyr Val Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Asp Val Ser Asn Arg Pro Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Ser Ser Tyr Thr Ser Ser Ser Thr Arg Val
1               5                   10

<210> SEQ ID NO 7
<211> LENGTH: 118
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

```
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Ile Lys Leu Gly Thr Val Thr Val Asp Tyr Trp Gly Gln Gly Thr
            100                 105                 110

Leu Val Thr Val Ser Ser
        115

<210> SEQ ID NO 8
<211> LENGTH: 110
<212> TYPE: PRT
<213> ORGANISM: Artificial Sequence
<220> FEATURE:
<223> OTHER INFORMATION: Synthetic Construct

<400> SEQUENCE: 8

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Val Phe Gly Thr Gly Thr Lys Val Thr Val Leu
            100                 105                 110

<210> SEQ ID NO 9
<211> LENGTH: 450
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Lys Leu Gly Thr Val Thr Val Asp Tyr Trp Gly Gln Gly
            100                 105                 110

Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
```

```
            130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 10
<211> LENGTH: 216
<212> TYPE: PRT
<213> ORGANISM: Artificial Sequence
<220> FEATURE:
<223> OTHER INFORMATION: Synthetic Construct

<400> SEQUENCE: 10

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
```

```
                35                          40                          45
Met Ile Tyr Asp Val Ser Asn Arg Pro Ser Gly Val Ser Asn Arg Phe
            50                          55                      60

Ser Gly Ser Lys Ser Gly Asn Thr Ala Ser Leu Thr Ile Ser Gly Leu
65                      70                      75                      80

Gln Ala Glu Asp Glu Ala Asp Tyr Tyr Cys Ser Ser Tyr Thr Ser Ser
                85                      90                      95

Ser Thr Arg Val Phe Gly Thr Gly Thr Lys Val Thr Val Leu Gly Gln
                100                     105                 110

Pro Lys Ala Asn Pro Thr Val Thr Leu Phe Pro Pro Ser Ser Glu Glu
            115                     120                 125

Leu Gln Ala Asn Lys Ala Thr Leu Val Cys Leu Ile Ser Asp Phe Tyr
    130                     135                 140

Pro Gly Ala Val Thr Val Ala Trp Lys Ala Asp Gly Ser Pro Val Lys
145                     150                 155                     160

Ala Gly Val Glu Thr Thr Lys Pro Ser Lys Gln Ser Asn Asn Lys Tyr
                165                     170                 175

Ala Ala Ser Ser Tyr Leu Ser Leu Thr Pro Glu Gln Trp Lys Ser His
            180                     185                 190

Arg Ser Tyr Ser Cys Gln Val Thr His Glu Gly Ser Thr Val Glu Lys
        195                     200                 205

Thr Val Ala Pro Thr Glu Cys Ser
    210                 215
```